United States Patent [19]

Tu et al.

[11] Patent Number: 5,719,273
[45] Date of Patent: Feb. 17, 1998

[54] PALLADIUM CATALYZED NUCLEOSIDE MODIFICATIONS METHODS USING NUCLEOPHILES AND CARBON MONOXIDE

[75] Inventors: Chi Tu, Louisville; Torin M. Dewey; Bruce Eaton, both of Boulder, all of Colo.

[73] Assignee: NeXstar Pharmaceuticals, Inc., Boulder, Colo.

[21] Appl. No.: 458,421

[22] Filed: Jun. 2, 1995

Related U.S. Application Data

[63] Continuation-in-part of Ser. No. 76,735, Jun. 14, 1993, Pat. No. 5,428,149.

[51] Int. Cl.$^6$ .................................................. C07H 19/00
[52] U.S. Cl. .................. 536/27.6; 536/27.6; 536/27.61; 536/27.62; 536/27.8; 536/27.81; 536/28.5; 536/28.51; 536/28.52; 536/28.53; 536/28.54; 536/28.55
[58] Field of Search ................... 536/28.1, 28.4, 536/28.5, 28.51, 28.52, 28.53, 28.54, 27.6, 27.61, 27.62, 27.8, 27.81

[56] References Cited

U.S. PATENT DOCUMENTS

| | | |
|---|---|---|
| 5,047,519 | 9/1991 | Hobbs, Jr. et al. . |
| 5,053,499 | 10/1991 | Kojima et al. . |
| 5,420,276 | 5/1995 | Norbeck .................... 544/310 |
| 5,428,149 | 6/1995 | Eaton . |

FOREIGN PATENT DOCUMENTS

| | | |
|---|---|---|
| 2 183 661 | 6/1987 | United Kingdom . |
| WO 89/06694 | 7/1989 | WIPO . |
| WO 90/15065 | 12/1990 | WIPO . |
| WO 91/06556 | 5/1991 | WIPO . |
| WO 91/06629 | 5/1991 | WIPO . |
| WO 91/10671 | 7/1991 | WIPO . |
| WO 91/14696 | 10/1991 | WIPO . |

OTHER PUBLICATIONS

Van Aerschot et al. Antiviral Activity of C-Alkylated Purine Nucleosides Obtained by Cross-Coupling with Tetraalkyltin Reagents, *Journal of Medicinal Chemistry*, 36:2938–2942 (1993).
Thiesen and Bach (1990) Nucleic Acids Research 18:3203.
Tronchet et al. (1988) Nucleosides & Nucleotides, 7:249.
Tuerk and Gold (1990) Science 249:505.
U.S. Patent App. Ser. No. 08/347,60, Tu and Eaton, filed Dec. 1, 1994, entitled "Purine Nucleoside Modifications by Palladium Catalyzed Methods".
Hacksell and Daes, Jr. (1983) J. Org. Chem. 48:2870.
Hobbs et al. (1973) Biochemistry 12:5138.
Ikehara and Tada (1968) in *Synthetic Procedures in Nucleic Acid Chemistry*, Zorbach, W.W.; Tipson, R.S. Eds.; John Wiley and Sons, NY; p. 189.
Joyce and Inoue (1989) Nucleic Acids Research 17:711.
Joyce (1989) Gene 82:83.
Kinzler and Vogelstein (1989) Nucleic Acids Research 17:3645.
Kramer et al. (1974) J. Mol. Biol. 89:719.
Levisohn et al. (1969) PNAS 63:805.
Levisohn et al. (1969) PNAS 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Pieken et al. (1991) Science 253:314.
Robertson and Joyce (1990) Nature 344:467.
Ruth and Bergstrom (1978) J. Org. Chem. 43:2870.
Sagi et al. (1994) J. Med. Chem. 37:1307.
Sessler et al. (1993) J. Am. Chem. Soc. 115:10418.
Shibahara et al. (1987) Nucliec Acids Res. 15:4403.
Sproat et al. (1989) Nucleic Acids Res. 17:3373.
Arai and Daves, Jr. (1978) J. Am. Chem. Soc. 100:287.
Bergstrom et al. (1981) J. Org. Chem. 46:1432.
Bergstrom and Ruth (1976) J. Am. Chem. Soc. 98:1587.
Bergstrom et al. (1982) J. Org. Chem. 47:2174.
Crisp (1989) Syn. Commun. 19:2117.
Dreyer and Dervan (1985) Proc. Natl. Acad. Sci. USA 82:968.
Ellington and Szostak (1990) Abstract of papers presented at the 1990 meeting on RNA Processing, Cold Spring Harbor Laboratory, Cold Spring Harbor, NY, p. 226.
Guschlbauer et al. (1977) Nucleic Acids Res. 4:1933.
Zhang et al., Organometallics, vol. 12, No. 5, pp. 1499–1500, (1993).
Fukuda et al., Z. fur Naturforschung, vol. 41(b), pp. 1571–1579, (1986).
Ono et al., Bioorganic & Medicinal Letters, vol. 4, NO. 2, pp. 361–366, (1994).
Agathocleous et al., J. Chem. Soc. Perkins Trans. pp. 2317–2321, (1991).

*Primary Examiner*—James O. Wilson
*Attorney, Agent, or Firm*—Swanson & Bratschun LLC

[57] ABSTRACT

This invention discloses a method for the preparation modified nucleosides using a palladium catalyst, a nucleophile and carbon monoxide.

43 Claims, No Drawings

PALLADIUM CATALYZED NUCLEOSIDE MODIFICATIONS METHODS USING NUCLEOPHILES AND CARBON MONOXIDE

CROSS REFERENCE TO RELATED APPLICATIONS

This applications is a Continuation-In-Part of U.S. patent application Ser. No. 08/076,735, filed Jun. 14, 1993, entitled Method for Palladium Catalyzed Carbon-Carbon Coupling and Products, now U.S. Pat. No. 5,428,149.

FIELD OF THE INVENTION

This invention relates to the field of nucleic acid chemistry, specifically to a process for preparing modified nucleosides. The nucleosides can be pyrimidines or purines. The pyrimidine compounds of the invention can be modified at the 5-, or 6-position of the pyrimidine ring. The purine compounds of the invention can be modified at the 2-, 6- or 8-position of the purine ring. Most preferably, the invention includes a process for preparing 8-position modified purine compounds and 5-position modified pyrimidine compounds. The present invention also includes the modified nucleosides produced by the method. The invention also includes the use of the modified nucleosides as anti-viral, anti-bacterial, anti-fungal or anti-neoplastic agents or as part of an oligonucleotide.

BACKGROUND OF THE INVENTION

Until quite recently, the consideration of oligonucleotides in any function other than strictly informational was not known. Despite the fact that certain oligonucleotides were known to have interesting structural possibilities (e.g., t-RNAs) and other oligonucleotides were bound specifically by polypeptides in nature, very little attention had been focused on the non-informational capacities of oligonucleotides. For this reason, among others, little consideration had been given to using oligonucleotides as pharmaceutical compounds. There are currently at least three areas of exploration that have led to serious studies regarding the use of oligonucleotides as pharmaceuticals. In the most advanced of the fields, antisense oligonucleotides are utilized to bind to certain coding regions in an organism to prevent the expression of proteins or to block various cell functions. The discovery of RNA species with catalytic functions—ribozymes—has led to the consideration of RNA species that serve to perform intracellular reactions that will achieve desired effects. And lastly, the discovery of the SELEX process (Systematic Evolution of Ligands by EXponential Enrichment) has shown the research community that oligonucleotides can be identified that will bind to almost any biologically interesting target.

The use of antisense oligonucleotides as a method for controlling gene expression and the potential for using oligonucleotides as pharmaceutical materials has prompted investigations into the introduction of a number of chemical modifications into oligonucleotides to increase their therapeutic activity. Such modifications are designed to increase cell penetration of the oligonucleotides, to stabilize them from nucleases and other enzymes that degrade or interfere with the structure or activity of the oligonucleotide analogs in the body, to enhance their binding to targeted nucleic acids, to provide a mode of disruption (terminating event) once sequence-specifically bound to targeted nucleic acids, and to improve their pharmacokinetic properties. For example, PCT Patent Application Publication WO 91/14696, entitled: Oligonucleotide-Transport Agent Disulfide Conjugates, describes a method for chemically modifying antisense oligonucleotides to enhance entry into a cell.

A variety of methods have been used to render oligonucleotides resistant to degradation by exonucleases. PCT Patent Application Publication WO 90/15065, entitled: Exonuclease-Resistant Oligonucleotides and Methods for Preparing the Same, describes a method for making exonuclease-resistant oligonucleotides by incorporating two or more phosphoramidite and phosphoromonothionate and/ or phosphorodithionate linkages at the 5' and/or 3' ends of the oligonucleotide. PCT Patent Application Publication WO 91/06629, entitled: Oligonucleotide Analogs with Novel Linkages, describes oligonucleotide compounds with one or more phosphodiester linkages between adjacent nucleotides replaced by a formacetal/ketal type linkage which are capable of binding RNA or DNA.

A common strategy for stabilization of RNA against endonucleolytic cleavage is to modify the 2'-position of ribonucleotides. Interference with base recognition by enzymes can be used to approach stabilization against base-specific endonucleolytic cleavage. Several strategies for this modification are known, including modification with 2'-amino and 2'-fluoro (Hobbs et al. (1973) Biochemistry 12:5138; Guschlbauer et al. (1977) Nucleic Acids Res. 4:1933), and 2'-$OCH_3$ (Shibahara et al. (1987) 15:4403; Sproat et al. (1989) Nucleic Acids Res. 17:3373). PCT Patent Application Publication WO 91/06556, entitled: 2' Modified Oligonucleotides, describes nuclease-resistant oligomers with substituents at the 2' position. PCT Patent Application Publication WO 91/10671, entitled: Compositions and Methods for Detecting and Modulating RNA Activity and Gene Expression, describes antisense oligonucleotides chemically modified at the 2' position and containing a reactive portion capable of catalyzing, alkylating, or otherwise effecting the cleavage of RNA, a targeting portion, and a tether portion for connecting the targeting and reactive portions.

The 5-position of pyrimidines may also be chemically modified. The introduction of modifications at the C-5 position of pyrimidines may be envisioned to interfere with the recognition by pyrimidine specific endonucleases. However, this concept is not as clear cut as the modification of the 2'-position of ribonucleotides.

The use of palladium to catalyze carbon-carbon bond formation at the 5 position of pyrimidine nucleosides is known. A superior method for 5-position modification of pyrimidines is described in U.S. Ser. No. 08/076,735, entitled "Method for Palladium Catalyzed Carbon-Carbon Coupling and Product," now U.S. Pat. No. 5,428,149 which is herein incorporated by reference in its entirety. The first examples of 5-position pyrimidine modifications were demonstrated by Bergstrom (Bergstrom et al. (1976) J. Am. Chem. Soc. 98:1587, (1978) J. Org. Chem. 43:2870, (1981) J. Org. Chem. 46:1432 and 2870, (1982) J. Org. Chem. 47:2174) and Daves (Arai and Daves (1978) J. Am. Chem. Soc., 100:287; Hacksell and Daves (1983) J. Org. Chem. 48:2870). Bergstrom and Daves used 5-mercurial-deoxyuridine compounds, the same as those used by Dreyer and Dervan ((1985) Proc. Natl. Acad. Sci. U.S.A. 82:968), to tether functional groups to oligonucleotides.

One method for simple carbon-carbon coupling reactions to the 5-position of uridines is described in the work of Crisp (1989) Syn. Commun. 19:2117. Crisp forms deoxyuridines functionalized at the 5-position by reacting protected 5-iodo-2'-deoxyuridine with alkenylstannanes in acetonitrile in the presence of a Pd (II) catalyst.

To date, very little work has been done to modify purine nucleosides using palladium catalysis. Van Aerschot et al., ((1993) J. Med. Chem 36:2938–2942) report that 2-, 6-, and 8-halogenated adenosines can be modified with symmetric organotin reagents. However, symmetric organotin compounds are not widely available. Sessler et al., ((1993) J. Am. Chem. 115:10418–10419) describe the arylation of protected 8-bromoguanosine with 4-tributyltinbenzaldehyde. However, using this procedure, a significant amount of starting material (28%) was unreacted. A superior method for modifying purine nucleosides using palladium catalysts is described in U.S. patent application Ser. No. 08/347,600, filed Dec. 1, 1994, entitled Purine Nucleoside Modification by Palladium Catalyzed Methods, which is herein incorporated by reference in its entirety.

Additionally, very little work has been done in the area of palladium catalyzed amidations. Schoenberg, et al. (J. Org. Chem. (1974) 39:3327) describe amidation of aryl and alkenyl halides, however, this work does not include nucleoside substrates or the use of a $PdL_4$ catalyst.

SELEX (Systematic Evolution of Ligands for EXponential Enrichment) is a method for identifying and producing nucleic acid ligands, termed "nucleic acid antibodies", e.g., nucleic acids that selectively bind to target molecules (Tuerk and Gold (1990) Science 249:505). The method involves selection from a mixture of candidates and step-wise iterations of structural improvement, using the same general selection theme, to achieve virtually any desired criterion of affinity and selectivity. Starting from a mixture of nucleic acids, the method includes steps of contacting the mixture with the target under conditions favorable for interaction, partitioning non-interacting nucleic acids from those nucleic acids which have interacted with the target molecules, dissociating the nucleic acid-target pairs, amplifying the nucleic acids dissociated from the nucleic acid-target pairs to yield a mixture of nucleic acids enriched for those which interact with the target, then reiterating the steps of interacting, partitioning, dissociating and amplifying through as many cycles as desired.

The methods of the present invention may be combined with SELEX to produce nucleic acids containing modified nucleotides. The presence of modified nucleotides may result in nucleic acids with an altered structure exhibiting an increased capacity to interact with target molecules. The steric and electronic influence of modified nucleosides may also act to prevent nuclease degradation.

BRIEF SUMMARY OF THE INVENTION

The present invention includes a novel method for introducing chemical moieties at various positions of nucleoside rings utilizing a palladium catalyst and a nucleophile and carbon monoxide. Preferably, the modifications are at the 5- or 6-position of a pyrimidine ring or at the 2-, 6-, or 8-positions of the purine ring. Most preferably the modifications are at the 5-position of the pyrimidine ring and at the 8-position of the purine ring. Particularly preferred modifications of the nucleoside ring include the introduction of an amide or ester moiety. For the preferred modifications, the nucleophile is a primary or secondary amine.

This invention includes a reaction scheme for producing a wide variety of modified nucleoside molecules. A key element in the production of the modified nucleosides is the use of a palladium catalyst in conjunction with a nucleophile and carbon monoxide.

More specifically, the invention provides a method for the preparation of a modified nucleoside comprising the steps of reacting a nucleoside starting material containing a leaving group attached to a carbon atom of the nucleoside starting material with a nucleophile and carbon monoxide in the presence of a palladium catalyst; and isolating the modified nucleoside. The modified nucleosides produced by this method are also included in the invention.

This invention further includes a method of preparing stabilized nucleic acids wherein the modified nucleoside is coupled to a sugar modified at the 2'-position or the 3'-position.

The modified nucleosides of the invention have many uses including, but not limited to, use as anti-viral, anti-bacterial, anti-fungal, or anti-neoplastic agents and use as part of an oligonucleotide.

DETAILED DESCRIPTION OF THE INVENTION

The present invention includes a method for modifying a nucleoside ring by reacting a nucleoside starting material with a nucleophile and carbon monoxide in the presence of a palladium catalyst. The invention includes the modifications of both pyrimidines and purines. The pyrimidines have the following structures and conventional numbering:

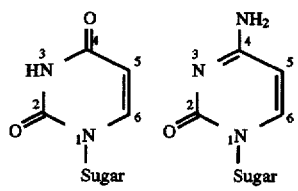

The pyrimidine ring can be modified at the 5- or 6-position; most preferably the 5-position is modified. The purines have the following structures and conventional numbering:

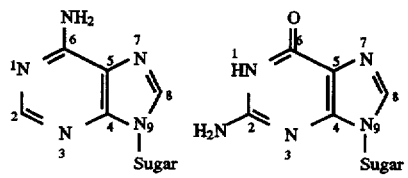

The purine can be modified at positions 2-, 6- and 8- of the purine ring; most preferably the 8-position is modified. Introduction of a variety of modifications to the nucleoside ring are contemplated by this invention. However, particularly preferred modifications to the nucleoside ring include the introduction of an amide or ester moiety. In the preferred modifications, the nucleophile for the carboxyamidation reaction is a primary or secondary amine.

The present invention extends to all novel compounds that can be prepared according to the methods of the present invention. The present invention also includes oligonucleotides that contain one or more of the novel substituted nucleosides of this invention. The present invention also includes the use of the modified nucleosides in various pharmaceutical areas, particularly anti-virals, anti-bacterials, anti-fungals and anti-neoplastics.

The general reactions of the present invention can be characterized as follows:

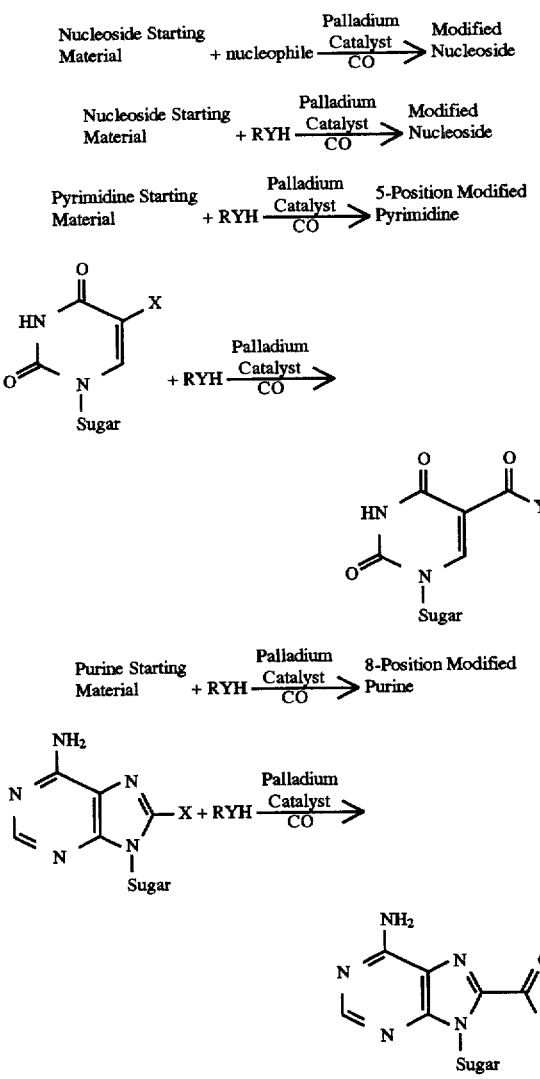

"Nucleoside starting material" is defined herein as any nucleoside base, nucleoside or nucleotide which has an attached acceptable leaving group (X). Nucleoside starting materials include all nucleosides, both naturally occurring and non-naturally occurring. Preferably, nucleoside starting materials include purines and pyrimidines, which include uracil, thymine, cytosine, adenine and guanine starting materials. The leaving group can be attached to any free carbon on the nucleoside or nucleoside base. The acceptable leaving group is displaced during the catalysis reaction and replaced by C(O)YR chemical moieties to yield the modified nucleoside or nucleoside base. The nucleoside starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Pyrimidine starting material" is defined herein as a pyrimidine base, pyrimidine nucleoside or pyrimidine nucleotide which has an attached acceptable leaving group (X). Pyrimidine starting materials include all pyrimidines, both naturally occurring and non-naturally occurring. Preferably, pyrimidine starting materials include uracil, thymine, and cytosine. The leaving group can be attached to any free carbon on the base of the nucleoside, preferably at the 5- or 6-position. The most preferred attachment is at the 5-position of the pyrimidine ring. The acceptable leaving group is displaced during the catalysis reaction and replaced by C(O)YR chemical moieties to yield the modified pyrimidine. The pyrimidine starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Purine starting material" is defined herein as a purine base, purine nucleoside or purine nucleotide which has an attached acceptable leaving group (X). Purine starting materials include adenine and guanine starting materials. The leaving group can be attached to any carbon atom of the base of the purine, preferably at the 2-, 6-, or 8-position of the purine ring. The most preferred attachment is at the 8-position. The acceptable leaving group is displaced during the catalysis reaction and replaced by C(O)YR chemical moieties to yield the modified purine. The purine starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Acceptable leaving group" is defined herein as a group which is a suitable counterion for palladium II, and is designated herein as X. In the most general embodiments of this invention, X is any of a number of acceptable leaving groups well known to those skilled in the art. Acceptable leaving groups include, but are not limited to, acetate, trifluoroacetate, trifluoromethyl sulfonate, tosylate, methane sulfonate and boronic esters and acids. In the preferred embodiment, X is a halogen, and in the most preferred embodiment X is bromine or iodine. The leaving group is attached to the carbon atom of the purine starting material by methods known to one of ordinary skill in the art.

"Nucleophile" is defined herein as would be understood by one of ordinary skill in the art. Specifically, a nucleophile is an electron rich chemical moiety capable of displacing a leaving group. Due to the nature of the catalytic reaction, the CO is inserted between said nucleoside starting material and said nucleophile. Anyone skilled in the art would recognize a useful nucleophile which could be used in a nucleophilic substitution reaction. Examples of preferred nucleophiles include, but are not limited to, amines, alcohols, and thiols.

The general structure of the nucleophiles used in the present invention is RYH, where Y=O, S, NH, or NR'. R and R' can optionally be part of a ring-structure, which can be aromatic, aliphatic or heterocyclic. In the preferred embodiments of the invention the nucleophile (RYH) is selected from the group consisting of aliphatic or aromatic, primary or secondary amines (including cyclic amines), alcohols and thiols; wherein R and R' are selected from the group consisting of substituted or unsubstituted C1–C20 alkyl (straight-chain or branched), C2–C20 alkenyl (straight-chain or branched), aryl, and natural and unnatural amino acids.

In a preferred embodiment, the nucleophile has the structure RYH, wherein,

Y is selected from the group consisting of O, S, and NH;

R is $(CH_2)_m(CH_3)_n$, wherein z is 0, 1, or 2; m is 0–19; n is 0, 1, 2, or 3; and wherein one or more of the H are optionally substituted with =O, —OH, =NH, $NH_2$.

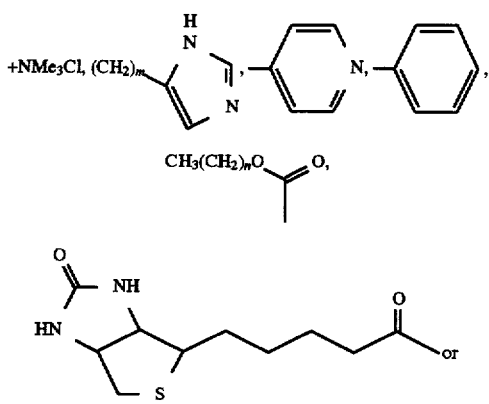

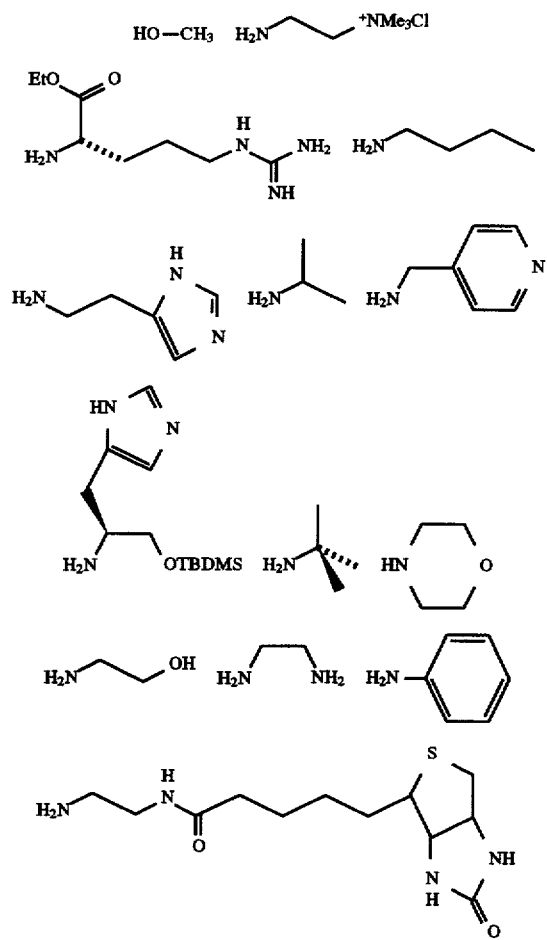

an amino acid.

In the most preferred embodiments of the invention, the nucleophiles are selected from the following group:

The R and R' groups of the nucleophile can include various functional groups which can be used to introduce a broad array of functional capabilities to the nucleosides prepared by this method. The nucleophile functional groups can include, among others: amides, esters, nitriles, nitros, ureas, halides, cyanates, alcohols, amines, ethers, thiols, aryl substituents, etc. as recognized by those of ordinary skill in the art. Any replacement of a hydrogen or functional group on the nucleophile is referred to as a "substitution" for the purposes of definition.

The palladium catalyst of the present invention may be characterized most generally as $PdL_4$ or $PdL_3$, where L is one of any number of commonly employed ligands of palladium. The palladium catalyst can be pre-made (e.g., $PdL_4$, wherein L is triphenyl phosphine, etc.) or made in situ from Pd(0) or Pd(II) as is known to one of ordinary skill in the art (e.g., [bis(benzylideneacetone)Pd(0)], $Pd(OAc)_2$, etc.). $PdL_4$ is the preferred palladium catalyst of the invention. It is within the skill and knowledge of those skilled in the art to recognize the various ligands that may be employed. Examples of common ligands (L) include, but are not limited to, $PPh_3$ (triphenyl phosphine), $(o\text{-tol})_3P$, $CH_3CN$, DMSO, N,N-dimethylformamide (DMF),

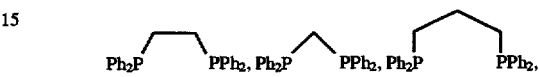

and

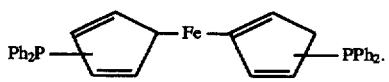

In the preferred embodiments of the catalytic species of this invention L=$PPh_3$ (triphenyl phosphine, or $P(C_6H_5)_3$). The preparation of certain catalysts of the present invention is described in U.S. Ser. No. 08/076,735, filed Jun. 14, 1993, entitled "Method for Palladium Catalyzed Carbon-Carbon Coupling and Products" which is incorporated by reference herein.

In certain embodiments, it may be advantageous to include additional basic, non-nucleophilic components in the reaction. Examples of desirable bases include, but are not limited to, $Et_3N$ and $EtN(iPr)_2$. Acceptable solvents for the reaction include acetonitrile, dioxane, acetone, ethyl acetate, benzene, dimethyl formamide, dimethyl acetamide, dimethyl sulfoxide, THF, hexamethylphosphoramide (HMPA), and hexamethylphosphoroustriamide (HMPT). The temperature ranges for the reaction typically are between 60 and 100 degrees centigrade, however, other suitable temperature ranges are also contemplated.

The modified nucleosides of the present invention are contemplated for use in oligonucleotides. Standard techniques for incorporation of nucleosides into oligonucleotides can be used with the modified nucleosides of the invention. The modified nucleosides are suitable for in vitro transcription procedures. The oligonucleotides containing the modified nucleosides have a number of various utilities. Specifically, the oligonucleotides interact with biological targets or have facilitating properties. The oligonucleotides can be useful in various diagnostic applications as well.

The nucleosides may also show antineoplastic, antibacterial, antifungal or antiviral activity. The nucleosides may also demonstrate other therapeutic properties. Standard assays are known to one of ordinary skill for determination of such activities. Formulation and administration routes are well known to those of ordinary skill in the art. Additionally, prodrug technology can be used as a delivery system for the nucleosides of the invention. Particularly, the nucleosides can be attached to lipids to improve pharmacology and oral availability, among other characteristics. Specifically, 5'-diacylglycero- or dialkylglycerophosphate-derivatives of the nucleosides of the invention are useful. These modified nucleosides are particularly interesting for antiviral applications. The diacylglycerophosphates of nucleosides and non-nucleosides have been used for modulation of pharmcokinetic behavior, modulation of bioavailability, and modulation of toxicity as described in U.S. Pat. No. 5,223,263 which is herein incorporated by reference.

Stability towards endo-nucleolytic degradation in serum can be achieved by introducing 2'-deoxy-2'-fluoro- or 2'-deoxy-2'-aminonucleosides to the pyrimidine positions of the ligand (Pieken et al. (1991) Science 253:314). The modified nucleosides of the present invention may also be coupled with 2' substituted species that would also be useful in a variety of situations. The incorporation of halogenated nucleosides may also prove valuable for enhanced ligand-target interaction.

EXAMPLES

The following examples are illustrative of preferred embodiments of methods of preparation and products of the invention and are not to be construed as limiting the invention thereto.

Example 1

Purine Modifications with Amines

The following general procedures were employed to produce the modified purines of Table I.

The general scheme:

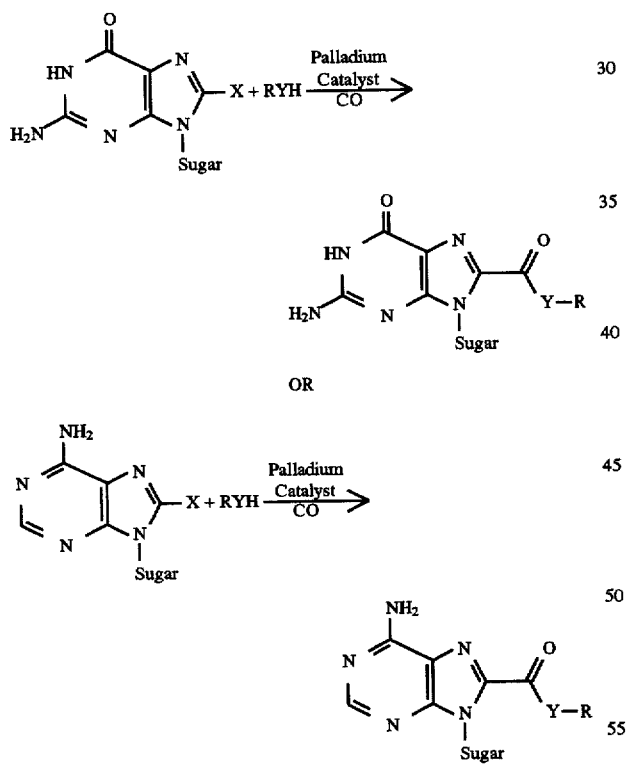

The more specific scheme:

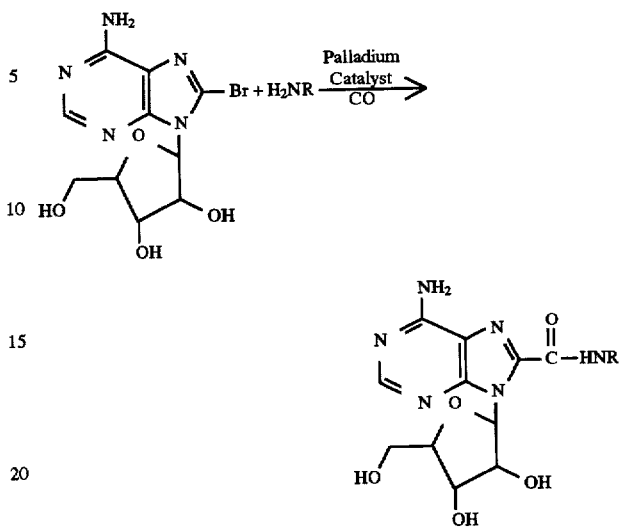

The various nucleoside base starting materials that can be used in the more specific scheme:

TABLE I

Examples of modified purine nucleosides.

| Entry | Nucleoside | Amine Nucleophile H₂NR | Product ID | Isolated Yield (%) |
|---|---|---|---|---|
| 1 | 1 | morpholine (HN-O ring) | 4 | 87[b] |
| 2 | 1 | 4-(aminomethyl)pyridine | 5 | 95 |
| 3 | 2 | 4-(aminomethyl)pyridine | 6 | 93 |
| 4 | 2 | H₂N-propyl (n-butylamine) | 7 | 84[a] |
| 5 | 2 | H₂N-CH(CH₃)₂ (isopropylamine) | 8 | 95 |
| 6 | 2 | H₂N-C(CH₃)₃ (tert-butylamine) | 9 | 98 |
| 7 | 2 | aniline (H₂N-C₆H₅) | 10 | 41 |
| 8 | 2 | H₂N-CH₂CH₂-N(Me)₃⁺Cl⁻ HCl | 11 | 91 |
| 9 | 2 | H₂N-CH₂CH₂-OH | 12 | 62[c] |
| 10 | 2 | ethyl arginate | 13 | 71 |
| 11 | 3 | H₂N-C(CH₃)₃ (tert-butylamine) | 14 | 85 |
| 12 | 3 | H₂N-CH₂CH₂-N(Me)₃⁺Cl⁻ HCl | 15 | 98 |
| 13 | 3 | ethyl arginate | 16 | 88 |
| 14 | 3 | 4-(aminomethyl)pyridine | 17 | 81 |

TABLE I-continued

Examples of modified purine nucleosides.

| Entry | Nucleoside | Amine Nucleophile H$_2$NR | Product ID | Isolated Yield (%) |
|---|---|---|---|---|
| 15 | 3 | (structure: biotin-derived amine with H$_2$N-CH$_2$CH$_2$-NH-C(=O)-(CH$_2$)$_4$-linked tetrahydrothiophene-imidazolone, i.e., N-(2-aminoethyl)biotinamide) | 18 | 56 |

*The reaction produced 16% of direct coupling side product.
ᵇThe reaction produced 15% of direct coupling side product.
ᶜThe reaction produced 14% of direct coupling side product and 14% of ester.

The following general procedures were followed to produce the modified purine nucleosides of Table I.

General.

The $^1$H and $^{13}$C NMR spectra were obtained in CD$_3$OD, D$_2$O, CDCl$_3$, or DMSO on a Bruker ARX-300 spectrometer using the deuterated solvent as an internal standard. Positive ion fast atom bombardment mass spectra (FAB$^+$) were performed at the Univ. of California at Berkeley Mass Spec. facility.

Materials.

8-Bromoadenosine, 8-bromoguanosine dihydrate, morpholine, n-butylamine, isopropylamine, tert-butylamine, aniline, 4-aminomethylpyridine, (2-aminoethyl) trimethylammonium chloride, arginine ethyl ester, ethanolamine, triethylamine, DMF and N,N-dimethylacetamide (DMA) were purchased from Aldrich Chemical Company and were used as received unless otherwise noted. N-(2-Aminoethyl)biotinamide hydrobromide was purchased from Molecular Probes, Inc.

General procedure for palladium catalyzed coupling reaction.

To a glass bomb with a Teflon valve was added the nucleoside specified in Table 1 (0.5 mmol), the amine nucleophile specified in Table 1 (1.0 mmol), Pd(PPh$_3$)$_4$ (0.0015 mmol), triethylamine (1.0 mmol) and DMF (or DMA). The glass bomb was evacuated and charged with CO (50 psi), then heated to the desired temperature for 24 hours. The solvent was removed and the residue was purified by flash chromatography on silica gel using a mixture of methanol in vacuo (5–30%) and methylene chloride, and/or recrystallization with methanol or isopropanol. The spectroscopic data for the coupling products follow.

Compound 4: 2',3',5'-Triacetyl-8-N-morpholine-adenosine carboxyamide

H NMR (DMSO/D$_2$O) δ 2.05 (s, 3H), 2.10 (s, 3H), 2.14 (s, 3H), 3.77 (m, 2H), 3.86 (m, 6H), 4.36 (m, 2H), 4.49 (m, 1H), 5.84 (t, J=6.3 Hz, 1H), 5.92 (s, 2H), 6.12 (dd, J=6.3, 4.0 Hz, 1H), 6.44 (d, J=4.0 Hz, 1H), 8.40 (s, 1H); $^{13}$C NMR (DMSO/D$_2$O) δ 20.5, 20.5, 20.7, 42.8, 47.9, 63.1, 66.6, 66.9, 70.4, 73.3, 79.9, 88.1, 118.3, 142.9, 150.1, 152.2, 155.1, 158.7, 169.6, 169.7, 170.6; MS (FAB) m/z (MH+)$^+$ 507.1838 (Calc. 507.1840 for C$_{21}$H$_{26}$N$_6$O$_9$+H$^+$).

Compound 5: 2',3',5'-Triacetyl-8-N-(4-methylpyridyl)-adenosine carboxyamide $^1$H NMR (CCl$_3$D) δ 2.03 (s, 3H), 2.09 (s, 3H), 2.14 (s, 3H), 4.38 (m, 2H), 4.49 (m,1H), 4.63 (d, J=6.2 Hz, 2H), 5.93 (s, 2H), 5.99 (t, J=6.5 Hz, 1H), 6.25 (dd, J=6.4, 3.6 Hz, 1H), 7.28 (d, J=4.3 Hz, 2H), 7.40 (d, J=3.4 Hz, 1H), 8.15 (t, J=6.3 Hz, 1H), 8.36 (s, 1H), 8.58 (d, J=4.8 Hz, 2H); $^{13}$C NMR (CCl$_3$D) δ 20.5, 20.7, 42.1, 63.3, 70.4, 73.2, 79.6, 88.0, 118.2, 122.2, 140.3, 146.5, 150.1, 151.0, 154.5, 156.2, 158.7, 169.6, 169.8, 170.1; MS (FAB) m/z (MH+)$^+$ 528.1842 (Calc. 528.1843 for C$_{23}$H$_{25}$N$_7$O$_8$+H$^+$).

Compound 6: 8-N-(4-Methylpyridyl)-adenosine carboxyamide $^1$H NMR (D$_2$O) d 3.72 (dd, J=12.5, 2.3 Hz, 1H), 3.88 (dd, J=10.5, 1.9 Hz, 1H), 4.16 (m, 1H), 4.37 (m, 1H), 4.65 (s, 2H), 4.98 (m, 1H), 7.14 (d, J=7.1 Hz, 1H), 7.43 (d, J=5.6 Hz, 2H), 8.18 (s, 1H), 8.47 (d, J=5.7 Hz, 2H); $^{13}$C NMR (DMSO/D$_2$) d 43.0, 64.1, 73.0, 74.7, 88.5, 91.3, 120.1, 124.0, 143.2, 150.2, 150.6, 151.5, 154.6, 158.8, 161.0; MS (FAB) m/z (M+1)$^+$ 402.1522 (Calc. 402.1526 for C$_{17}$H$_{19}$N$_7$O$_5$+H$^+$).

Compound 7: 8-N-(n-Butyl)-adenosine carboxyamide $^1$H NMR (DMSO) δ 0.91 (t, J=7.2 Hz, 3H), 1.34 (m, 2H), 1.52 (m, 2H), 3.31 (t, J=7.2 Hz, 1H), 3.53 (m, 1H), 3.68 (m, 2H), 3.95 (d, J=2.7 Hz, 1H), 4.20 (m, 1H), 4.96 (dd, J=12.0, 6.4 Hz, 1H), 5.13 (d, J=4.4 Hz, 1H), 5.25 (d, J=6.4 Hz, 1H), 5.59 (dd, J=8.9, 3.4 Hz, 1H), 6.69 (d, J=6.7 Hz, 1H), 7.60 (s, 2H), 8.18 (s, 1H), 8.73 (t, J=5.8 Hz, 1H); $^{13}$C NMR (DMSO) δ 23.2, 29.1, 40.5, 48.1, 71.8, 80.4, 81.3, 95.8, 98.6, 127.4, 152.2, 159.5, 162.9, 166.4, 168.2; MS (FAB) m/z (MH+)$^+$ 367.1723 (Calc. 367.1729 for C$_{15}$H$_{23}$N$_6$O$_5$+H$^+$).

Compound 8: 8-N-(2-Propyl)-adenosine carboxyamide $^1$H NMR (CD$_3$OD) δ 1.27 (d, J=6.5 Hz, 6H), 3.73 (dd, J=12.5, 2.6 Hz, 1H), 3.89 (dd, J=12.5, 2.2 Hz, 1H), 4.17 (m, 1H), 4.21 (q, J=6.5 Hz, 1H), 4.37 (dd, J=5.3, 1.9 Hz, 1H), 4.96 (dd, J=6.9, 4.3 Hz, 1H), 7.07 (d, J=7.2 Hz, 1H), 8.19 (s, 1H); $^{13}$C NMR (CD$_3$OD) δ 22.5, 43.1, 64.1, 72.9, 74.7, 88.4, 91.3, 119.9, 144.0, 151.4, 154.4, 158.7, 159.8; MS (FAB) m/z (M+1)$^+$ 353.1574 (Calc. 353.1573 for C$_{14}$H$_{20}$N$_6$O$_5$+H$^+$).

Compound 9: 8-N-t(-Butyl)-adenosine carboxyamide $^1$H NMR (DMSO/D$_2$O) δ 1.37 (s, 9H), 3.52 (dd, J=12.3, 3.7 Hz, 1H), 3.66 (dd, J=12.5, 3.1 Hz, 1H), 3.94 (m, 1H), 4.18 (m, 1H), 4.91 (t, J=5.5 Hz, 1H), 6.74 (d, J=6.8 Hz, 1H), 8.15 (s, 1H); $^{13}$C NMR (DMSO/D$_2$O) δ 28.7, 52.0, 62.7, 71.3, 72.4, 86.7, 89.5, 118.1, 143.2, 150.4, 153.9, 157.2, 158.6; MS (FAB) m/z (M+1)$^+$ 367.1723 (Calc. 367.1717 for C$_{15}$H$_{22}$N$_6$O$_5$+H$^+$).

Compound 10: 8-N-Phenyl-adenosine carboxyamide $^1$H NMR (DMSO/D$_2$O) δ 3.74 (dd, J=12.5, 2.6 Hz, 1H), 3.91 (dd, J=12.6, 2.3 Hz, 1H), 4.19 (m, 1H), 4.39 (dd, J=5.4, 2.0 Hz, 1H), 4.99 (dd, J=7.1, 5.5 Hz, 1H) 7.18 (m, 2H), 7.39 (t, J=5.6 Hz, 2H), 7.74 (d, J=5.6 Hz, 2H), 8.21 (s, 1H); $^{13}$C NMR (DMSO) δ 62.2, 70.9, 71.9, 86.4, 89.1, 118.0, 120.0, 124.5, 128.9, 138.0, 142.7, 150.1, 153.7, 157.0, 157.3; MS (FAB) m/z (M+1)$^+$ 387.1419 (Calc. 387.1417 for C$_{17}$H$_{18}$N$_6$O$_5$+H$^+$).

Compound 11: 8-N-((2-Aminoethyl)trimethylammonium chloride)-adenosine carboxyamide $^1$H NMR (CD$_3$OD) δ 3.27 (s, 9H), 3.65 (t, J=6.4 Hz, 2H), 3.73 (dd, J=12.5, 2.5 Hz, 1H), 3.90 (m, 3H), 4.17 (m, 1H), 4.36 (dd, J=5.3, 1.7 Hz, 1H), 4.96 (dd, J=7.1, 5.4 Hz, 1H), 7.16 (d, J=7.2 Hz, 1H), 8.19 (s, 1H); $^{13}$C NMR (CD$_3$OD) δ 35.0, 54.1, 64.1, 65.6, 73.0, 74.6, 88.7, 91.1, 120.1, 142.7, 151.5, 154.7, 158.9, 161.1; MS (FAB) m/z (M-Cl$^-$)$^+$ 396.1995 (Calc. 396.1995 for C$_{16}$H$_{26}$N$_7$O$_5$-Cl$^-$).

Compound 12: 8-N-(2-hydroxyethy)-adenosine carboxyamide $^1$H NMR (DMSO/D$_2$) δ 3.35 (m, 2H), 3.53 (m,3H), 3.67 (dd, J=12.5, 3.1 Hz, 1H), 3.96 (m, 1H), 4.17 (m, 1H), 4.89 (t, J=5.9 Hz, 1H),6.86 (d, J=6.8 Hz, 1H) 8.15 (s, 1H); $^{13}$C NMR (DMSO/D$_2$O) δ 42.0, 59.8, 62.7, 71.3, 72.4, 86.7, 89.5, 118.0, 142.4, 150.5, 154.0, 157.3159.7; MS (FAB) m/z (M+1)$^+$ 355.1372 (Calc. 355.1366 for C$_{13}$H$_{18}$N$_6$O$_6$+H$^+$).

Compound 13: 8-N-(Arginine ethyl ester)-adenosine carboxyamide $^1$H NMR (CD$_3$OD) δ 1.28 (t, J=7.1 Hz, 3H), 1.75 (m, 2H), 1.96 (m, 1H), 2.07 (m, 1H), 3.27 (m, 2H), 3.73 (dd, J=12.6, 2.7 Hz, 1H), 3.88 (dd, J=12.6, 2.3 Hz, 1H), 4.18 (m, 1H), 4.23 (q, J=7.1 Hz, 2H), 4.41 (dd, J=5.4, 1.9 Hz, 1H), 4.67 (dd, J=8.9, 5.0 Hz, 1H), 5.01 (dd, J=7.0, 5.5 Hz, 1H), 7.09 (d, J=7.1 Hz, 1H), 8.17 (s, 1H); $^{13}$C NMR (D$_2$O/CD$_3$OD) δ 14.4, 25.6, 28.7, 41.5, 53.8, 63.1, 63.9, 72.0, 74.0, 87.5, 90.3, 119.2, 142.4, 150.4, 154.4, 157.4, 157.7, 160.1, 174.0: MS (FAB) m/z (M+1)$^+$ (Calc. 387.1417 for C$_{17}$H$_{18}$N$_6$O$_5$+H$^+$).

Compound 14: 8-N-(t-Butyl)-guanosine carboxyamide $^1$H NMR (CD$_3$OD) δ 1.44 (s, 9H), 3.74 (dd, J=12.2, 3.7 Hz, 1H), 3.86 (dd, J=12.2, 2.9 Hz, 1H), 4.07 (m, 1H), 4.39 (dd, J=5.8, 3.4 Hz, 1H), 4.95 (t, J=6.0 Hz, 1H), 6.93 (d, J=6.4 Hz, 1H); $^{13}$C NMR (DMSO/D$_2$O) δ 28.9, 52.9, 64.0, 72.4, 73.8, 87.4, 91.1, 117.5, 141.6, 154.1, 155.5, 159.7, 159.9; MS (FAB) m/z (M+1)$^+$ 383.1676 (Calc. 383.1679 for C$_{15}$H$_{22}$N$_6$O$_6$+H$^+$).

Compound 15: 8-N-((2-Aminoethyl)trimethylammonium chloride)-guanosine carboxyamide $^1$H NMR (D$_2$O) d 3.24 (s, 9H), 3.64 (t, J=6.6 Hz, 2H), 3.91 (m, 4H), 4.20 (m, 1H), 4.52 (dd, J=5.1, 3.7 Hz, 1H), 5.05 (t, J=6.0 Hz, 1H), 6.85 (d, J=6.2 Hz, 1H); $^{13}$C NMR (CD$_3$OD) d 34.6, 54.4, 63.0, 65.0, 71.7, 73.1, 86.6, 90.1, 117.6, 140.1, 153.9, 155.1, 160.5, 161.1; MS (FAB) m/z (M-Cl$^-$)$^+$ 412.1950 (Calc. 412.1945 for C$_{16}$H$_{26}$N$_7$O$_6$-Cl$^-$).

Compound 16: 8-N-(Arginine ethyl ester)-guanosine carboxyamide $^1$H NMR (CD$_3$OD) δ 1.28 (t, J=7.1 Hz, 3H), 1.72 (m, 2H), 1.89 (m, 1H), 2.03 (m, 1H), 3.23 (m, 2H), 3.74 (dd, J=12.1, 3.8 Hz, 1H), 3.86 (dd, J=12.2, 2.9 Hz, 1H), 4.06 (m, 1H), 4.21 (q, J=7.1, Hz, 2H), 4.39 (dd, J=5.7, 2.4 Hz, 1H), 4.61 (dd, J=9.1, 4.7 Hz, 1H), 4.98 (t, J=6.0 Hz, 1H), 6.98 (d, J=6.3 Hz, 1H); MS (FAB) m/z (M+1)$^+$ 512.2219 (Calc. 512.2217 for C$_{19}$H$_{20}$N$_9$O$_8$+H$^+$).

Compound 17: 8-N-(4-Methylpyridyl)-guanosine carboxyamide $^1$H NMR (DMSO/D$_2$O) δ 3.51 (m, 1H), 3.64 (dd, J=11.9, 4.4 Hz, 1H), 3.79 (m, 1H), 4.17 (dd, J=5.5, 4.3 Hz, 1H), 4.42 (d, J=6.3 Hz, 2H), 4.91 (t, J=5.8 Hz, 1H), 6.62 (s, 2H), 6.71 (d, J=5.76 Hz, 1H), 7.29 (d, J=5.7 Hz, 2H), 8.49 (d, J=5.3 Hz, 2H), 9.45 (t, J=6.2 Hz, 1H); $^{13}$C NMR (DMSO/D$_2$O) δ 41.3, 62.2, 70.4, 71.1, 85.4, 89.0, 116.3, 122.3, 138.3, 148.4, 149.6, 152.8, 153.7, 156.7, 159.1; MS (FAB) m/z (M+1)$^+$ 418.1482 (Calc. 418.1488 for C$_{19}$H$_{21}$N$_4$O$_7$+H$^+$).

Compound 18: 8-N-(2-Aminoethyl biotinamide)-guanosine carboxyamide $^1$H NMR (CD$_3$OD) δ 1.17 (m, 2H), 1.26 (t, J=12.0 Hz, 2H), 1.39 (m, 1H), 1.50 (m, 3H), 2.23 (t, J=12.5 Hz, 2H), 2.63 (d, J=22 Hz, 1H), 2.80 (dd, J=22, 8.0 Hz, 1H), 2.90 (m, 1H), 3.18 (m, 2H), 3.48 (m, 4H), 3.81 (dd, J=19.5, 6.0 Hz, 1H), 3.91 (dd, J=11.5, 4.0 Hz, 1H), 4.08 (m, 1H), 4.19 (m, 1H), 4.40 (m, 1H), 4.47 (m, 1H), 4.96 (t, J=10 Hz, 1H), 6.83 (d, J=11 Hz, 1H); The solubility of compound 18 is too low in DMSO to obtained a good C13 spectrum; MS (FAB) m/z (M+1)$^+$ 596.2251 (Calc. 596.2264 for C$_{23}$H$_{33}$N$_9$O$_8$S+H$^+$).

Example 2

Purine Modification with Alcohols

The general procedure outline in Example 1 was followed to produce the modified purine described by the following scheme with the following results.

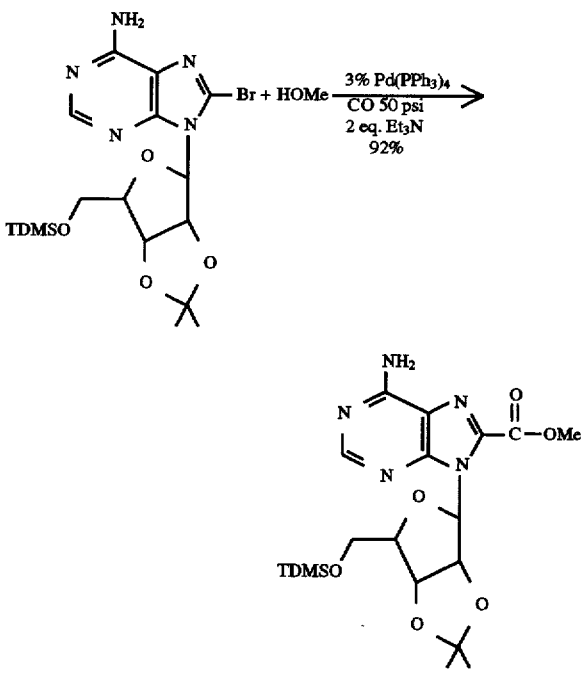

$^1$H NMR (DMSO/D$_2$O) δ −0.05 (s, 3H), −0.04 (s, 3H), 0.82 (s, 9H), 1.38 (s, 3H), 1.60 (s, 3H), 3.67 (dd, J=10.5, 6.5 Hz, 1H), 3.78 (dd, J=10.6, 6.5 Hz, 1H), 4.03 (s, 3H), 4.25 (m, 1H), 5.10 (dd, J=6.5, 3.8 Hz, 1H), 5.69 (dd, J=6.4, 2.1 Hz, 1H), 6.34 (s, 2H), 7.04 (d, J=2.2 Hz, 1H), 8.36 (s, 1H).

Example 3

Pyrimidine Modifications with Amines

The following procedures were employed to produce the modified pyrimidine nucleosides described in Table 2. The general scheme:

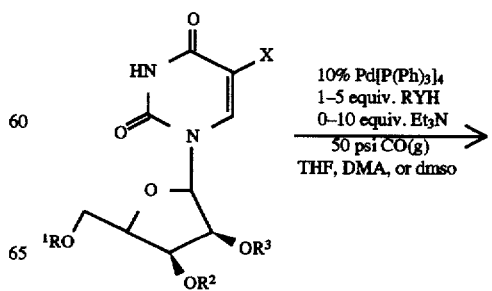

17
-continued

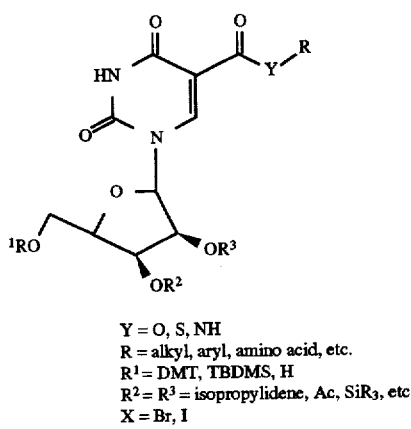

Y = O, S, NH
R = alkyl, aryl, amino acid, etc.
R¹ = DMT, TBDMS, H
R² = R³ = isopropylidene, Ac, SiR₃, etc.
X = Br, I Specific Scheme:

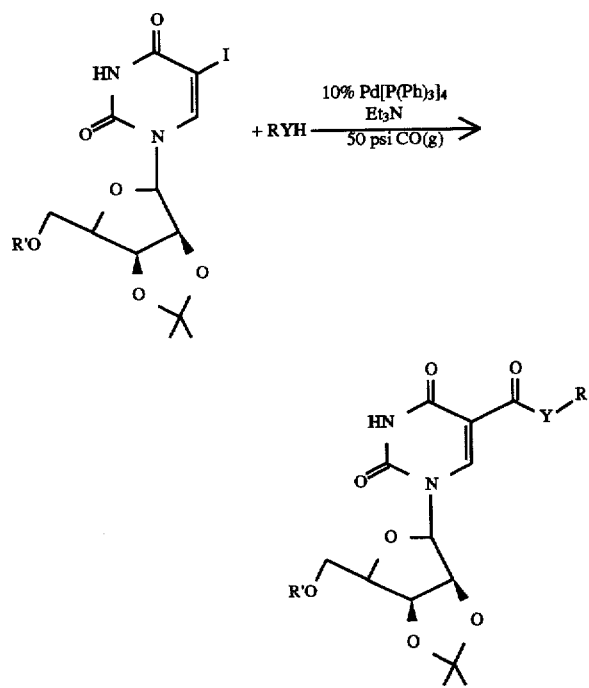

19, R' = H
20, R' = DMT
21, R' = TBDMS

RYH

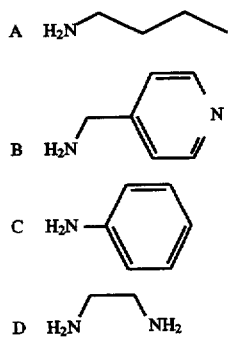

18
-continued

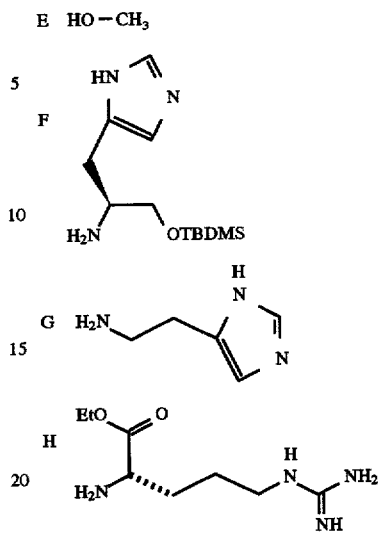

TABLE II

Summary of uridine carboxyamidation products.

| Entry | Nucleoside starting material | RYH | Product ID | Isolated Yield (%) |
|---|---|---|---|---|
| 1 | 19 | A | 22 | 65% |
| 2 | 19 | B | 23 | 89% |
| 3 | 19 | C | 24 | 20% |
| 4 | 19 | D | 25 | 78% |
| 5 | 20 | E | 26 | <20% |
| 6 | 21 | E | 27 | <20% |
| 7 | 20 | F | 28 | 69% |
| 8 | 21 | G | 29 | 68% |
| 9 | 21 | H | 30 | 57% |

Starting Material Syntheses.

The starting materials (Compounds 19–21) were synthesized by the following procedures.

Compound 19. 5-iodo-2',3'-isopropylideneuridine.

To a stirred solution of 5.0 g of 5-iodouridine (13.5 mmol) in 300 mL of acetone was added 250.0 mg of p-toluenesulfonic acid (1.3 mmol). The flask was fitted with an addition funnel filled with 4 Å molecular sieves and a reflux condenser. The solution was heated at reflux temperature for 2 h., after which all solids had dissolved. The flask was allowed to cool to room temperature and the solution concentrated in vacuo. The solution was dissolved in acetone, filtered through a plug of silica and the filtrate concentrated to give a pale yellow solid. This material was re-crystallized from ethanol to give the product as white needles in quantitative yield.

Compound 20. 5'-DMT-5-iodo-2',3'-isopropylideneuridine.

To a stirred solution of 820.3 mg of 5-iodo-2',3'-isopropylideneuridine (2.0 mmol) in 1.0 mL of anhydrous DMF and 1.8 mL of anhydrous pyridine, under argon, was added 24.4 mg of 4-dimethylaminopyridine (0.2 mmol) and 745.4 mg of DMTCl (2.2 mmol). The solution was stirred at room temperature overnight, diluted with 150 mL of ethyl acetate, washed with 3×75 mL H₂O, 1×50 mL brine and concentrated in vacuo. The residue was purified by flash chromatography on silica gel with 40% EtOAc/hexanes to give 1.282 g (90% yield) of the product as a white solid.

Compound 21. 5'-TBDMS-5-iodo-2',3'-isopropylideneuridine.

To a stirred solution of 1.00 g of 5-iodo-2',3'-isopropylideneuridine (2.4 mmol) in 1.9 mL of anhydrous pyridine was added 724 mg of TBDMSCl (4.8 mmol). The solution was stirred overnight at room temperature, diluted with 30 mL of ethyl acetate and washed with 3×20 mL $H_2O$, 1×20 mL brine and concentrated in vacuo. The residue was purified by flash chromatography on silica gel with 30% EtOAc/hexanes to give 1.153 g (91% yield) of the product as a white solid.

Modified Pyrimidine Syntheses

The modified pyrimidines described in Table II were synthesized as follows.

Compound 22. 5-(N-Butylcarboxyamide)-2',3'-isopropylideneuridine.

To a 300 mL stainless steel Parr bomb in an argon atmosphere glove box was added a solution of 2',3'-isopropylidene-5-iodouridine (0.351 g, 1.00 mmol, in 3.0 mL of THF), 10 mL of 1.0M $Et_3N$/THF (10.0 mmol), 3.0 mL of 1.0M n-butylamine in THF (3.0 mmol), and tetrakis(triphenyl-phosphine)palladium (0.1156 g, 0.10 mmol). The bomb was sealed, removed from the box, evacuated and charged three times with 100 psi CO, then heated at 70° C. for 24 h. The bomb was allowed to cool to room temperature, vented carefully in a fume hood, and the solvent removed in vacuo. The crude reaction material was purified by flash chromatography on silica gel with 5% MeOH/$CH_2Cl_2$ to give the product as a yellow solid (0.251 g, 65% yield). Analytical samples were obtained by crystallization from MeOH to give the pure product as fluffy white needles. $^1H$ NMR (dmso-$d_6$) δ 11.92 (br s, 1H), 8.68 (t, J=5.4 Hz, 1H), 8.61 (s, 1H), 5.85 (d, J=1.8 Hz, 1H), 5.09 (t, J=4.5 Hz, 1H), 4.91 (dd, J=6.3, 1.8 Hz, 1H), 4.74 (dd, J=6.0, 2.7 Hz, 1H), 4.19 (m, 1H), 3.56 (m, 2H), 3.24 (m, 2H), 1.47 (s, 3H), 1.4 (m, 2H), 1.3 (m, 2H), 1.27 (s, 3H), 0.9 (t, J=7.2 Hz, 3H); $^{13}C$ NMR (dmso-$d_6$) δ 163.3 (C4), 161.3 (CONHBu), 149.4 (C2), 146.9 (C6), 112.5 (CMe$_2$), 105.0 (C5), 92.8 (C1'), 87.4 (C4'), 84.4 (C2') 8.07 (C3'), 61.2 (C5'), 38.0 (CONHCH$_2$—), 31.2,(NHCH$_2$CH$_2$—), 26.9 (CCH$_3$), 25.0 (CCH$_3$), 19.5 (NHCH$_2$CH$_2$CH$_2$CH$_3$), 13.6 (NHCH$_2$CH$_2$CH$_2$CH$_3$); HRMS: Calculated (observed) for $C_{17}H_{26}N_3O_7$: 384.1771(384.1772). Anal. calcd. (found) for $C_{17}H_{25}N_3O_7$: C, 53.26(53.46); H, 6.57(6.53); N, 10.96 (10.98).

Compound 23. 5-[N-(4-pyridylmethyl)carboxyamide]-2',3'-isopropylideneuridine.

To a heavy-walled glass bomb was added 224 mg 2',3'-isopropylidene-5-iodouridine (0.542 mmol), 63 mg tetrakis (triphenylphosphine)palladium (0.0542 mmol) and anhydrous pyridine until the solids were dissolved. Pyridine was then removed in vacuo and the solids dried under high vacuum overnight. To the bomb was then added, under argon, 4 mL anhydrous THF, 0.75 mL triethylamine (5.42 mmol) and 0.22 mL 4-aminomethylpyridine (2.17 mmol). The bomb was evacuated and charged three times with CO and heated to 70° C. for 2.5 days. The bomb was allowed to cool to room temperature, the solvent removed in vacuo and the crude material loaded onto a pad of silica with dichloromethane. The pad was eluted with dichloromethane, then the desired product eluted with 10% MeOH/$CH_2Cl_2$ and concentrated in vacuo to a pale yellow solid. This material was purified by flash chromatography on silica gel with 5% MeOH/$CH_2Cl_2$ to give 201 mg (89% yield) of the product as a pale yellow solid. This material was recrystallized from methanol to give analytical samples of pure product as white needles.

$^1H$ NMR (dmso-$d_6$) δ 11.98 (s, 1H), 9.19 (t, J=6.3 Hz, 1H), 8.66 (s, 1H), 8.48 (d, 2H, J=4.5 Hz), 7.25 (d, J=5.7 Hz, 2H), 5.86 (d, J=2.2 Hz, 1H), 5.10 (t, J=4.8 Hz, 1H), 4.93 (dd, J=6.2, 2.2 Hz, 1H), 4.73 (dd, J=6.3, 3.0 Hz, 1H), 4.49 (d, J=6.3 Hz, 2H), 4.20 (m, 1H), 3.56 (t, J=4.5 Hz, 2H), 1.47 (s, 3H), 1.27 (s, 3H). $^{13}C$ NMR (dmso-$d_6$) δ 163.2 (C4), 161.9 (CONH—), 149.5 (pyr o-C), 149.4 (C2), 148.4 (pyr p-C), 147.4 (C6), 122.1 (pyr m-C), 112.6 (CMe$_2$), 104.8 (C5), 92.9 (C1'), 87.4 (C4'), 84.4 (C2'), 80.7 (C3'), 61.2 (C5'), 41.2 (NHCH$_2$—), 26.9 (CCH$_3$), 25.0 (CCH$_3$); HRMS: Calculated (observed) for $C_{19}H_{23}N_4O_7$: 419.1567(419.1569). UV spectrum: $v_{max}$ at 276 nm (ε=13730 $M^{-1}cm^{-1}$).

5-[N-(4-pyridylmethyl)carboxyamide]-2',3'-isopropylidene-5'-triphosphate-uridine.

The 5'-hydroxyl compound prepared as described was converted to the 5'-triphosphate using the procedure of Eckstein. The crude triphosphate was purified successively on DEAE sephadex anion exchange resin and C18 RP-HPLC using 100 mM $Et_3NH^+HCO_3^-$ and $CH_3CN$ as the mobile phases. The purity of the compound was checked by analytical C18 RP-HPLC, $^1H$ and $^{31}P$ NMR ($D_2O$), and quantitated by its UV absorbance at 276 nm (ε=13700$M^-$ $1cm^{-1}$).

Compound 24. 5-(N-phenylcarboxyamide)-2',3'-isopropylideneuridine.

To a heavy-walled glass bomb in an argon atmosphere glove box was added 2',3'-isopropylidene-5-iodouridine (0.261 g, 0.636 mmol), tetrakis(triphenylphosphine) palladium (0.083 g, 0.072 mmol), and 4.5 mL of 1.0M $Et_3N$/THF (4.5 mmol). The bomb was sealed, removed from the box, and 0.3 mL of aniline added via syringe under argon. The flask was evacuated and charged three times with 50 psi CO and heated to 70° C. for 2 days. The bomb was cooled to room temperature, concentrated in vacuo and purified by flash chromatography on silica gel with 4–6.5% MeOH.NH$_3$/$CH_2Cl_2$ to give a slightly yellow solid. This material was re-crystallized from methanol to give 52 mg (20% yield) of the pure product as fine white needles. $^1H$ NMR (dmso-$d_6$) δ 12.16 (br s, 1H), 10.88 (s, 1H), 8.79 (s, 1H), 7.63 (d, J=7.8 Hz, 2H), 7.34 (m, 2H), 7.09 (t, J=7.4 Hz, 1H), 5.88 (d, J=2.1 Hz, 1H), 5.16 (t, J=4.7 Hz, 1H), 4.95 (dd, J=6.3, 2.1 Hz, 1H), 4.76 (dd, J=6.3, 2.7 Hz, 1H), 4.25 (m, 1H), 3.59 (m, 2H), 1.48 (s, 3H), 1.29 (s, 3H); $^{13}C$ NMR (dmso-$d_6$) δ 163.6 (C4), 159.9 (CONH—), 149.3 (C2), 147.8 (C6), 138.1 (CONHC<), 129.0 (phenyl m-C), 124.0 (phenyl p-C), 119.5 (phenyl o-C), 112.5 (CMe$_2$), 104.6 (C5), 93.2 (C1'), 87.6 (C4'), 84.5 (C2'), 80.7 (C3'), 61.2 (C5'), 26.9 (CCH$_3$), 25.0 (CCH$_3$). HRMS: Calculated (observed) for $C_{19}H_{22}N_3O_7$: 404.1458(404.1468).

Compound 25. 5'-TBDMS-5-(N-[2-(N'-trifluoroacetamido) ethyl]carboxyamide)-2',3'-isopropylideneuridine.

To a heavy-walled glass bomb in an argon atmosphere glove box was added 5'-TBDMS-2',3'-isopropylidene-5-iodouridine (0.531 g, 1.01 mmol), tetrakis (triphenylphosphine)palladium (0.350 g, 0.303 mmol), $Et_3N$ (0.704 mL, 5.05 mmol) and 2 mL of dry THF. The bomb was sealed, removed from the box and 0.203 mL ethylenediamine (3.03 mmol) added under positive argon flow. The bomb was sealed under argon, evacuated and charged three times with 50 psi CO and heated to 70° C. overnight. The bomb was allowed to cool to room temperature, vented slowly, the solvent removed in vacuo and the crude material purified by flash silica gel chromatography with 25% MeOH.NH$_3$/EtOAc to give 381.0 mg (78% yield) of the product as a white solid. This material was protected as the N-triflouroacetamide in the following manner. To a stirred solution of 381.0 mg of the above product (0.78 mmol) in 7.0 mL of anhyd. $CH_2Cl_2$ at 0° C. was added dry pyridine (0.126 mL, 1.6 mmol) and $(CF_3CO)_2O$ (0.13 mL, 0.94 mmol). The solution was stirred at 0° C. for 30 min. then 0.19 mL of (CF$_3$CO)$_2$O (1.33 mmol) and 0.13 mL of pyridine (1.66 mmol) was added. After 30 min. the reaction was allowed to warm to room temperature, concentrated in vacuo and purified by flash silica gel chromatography with 40% EtOAc/hexanes to give 173.5 mg (38% yield, 30% yield from iodouridine starting material) of the product as a white solid.

$^1$H NMR (dmso-d$_6$) δ 11.95 (s, 1H), 9.48 (t, J=5.0 Hz, 1H), 8.81 (t, 5.8 Hz, 1H), 8.49 (s, 1H), 5.75 (d, J=1.6 Hz, 1H), 4.89 (dd, J=6.1, 1.7 Hz, 1H), 4.67 (dd, J=6.1, 2.2 Hz, 1H), 4.36 (m, 1H), 3.77 (m, 2H), 3.4 (m, 2H), 3.3 (m, 2H), 1.48 (s, 3H), (s, 3H), 1.29 (s, 3H), 0.78 (s, 9H), 0.00 (s, 3H), −0.04 (s, 3H); $^{13}$C NMR (dmso-d$_6$) δ 163.1 (C4), 162.0 (CONH—), 149.4 (C2), 147.0 (C5), 117.7, 113.9, 112.2, 104.4, 94.7, 87.8, 85.0, 81.0, 63.4, 38.1, 37.2, 26.8, 25.6, 24.9, 17.8, −5.8, −5.8. HRMS: Calculated (observed) for C$_{23}$H$_{36}$F$_3$N$_4$O$_8$Si: 581.2254(581.2249).

Compound 26. 5'-DMT-5-carbomethoxy-2',3'-isopropylideneuridine.

In a glove box 5'-DMT-5-iodouridine (1.0 mL of a solution of 0.10 g/mL, 0.14 mmol) was added to a small heavy-walled glass bomb. Solid tetrakis(triphenylphosphine)palladium (16.2 mg, 0.014 mmol) was added, followed by 0.7 mmol of Et$_3$N as a 1.0M solution in THF, and 3.0 mL of anhydrous methanol (distilled in vacuo over Mg). The bomb was evacuated and refilled with 50 psi of CO (3×), then sealed and heated to 70° C. with stirring for 3 days. The vessel was vented and the solvents removed in vacuo, and the residue dissolved in the minimum 5% MeOH/CH$_2$Cl$_2$ and loaded onto a pad of silica gel, and eluted successively with CH$_2$Cl$_2$ (discarded) and 5% MeOH/CH$_2$Cl$_2$. The resultant material was flash chromatographed on silica gel with 5% MeOH/CH$_2$Cl$_2$ to give the product as a colorless solid. $^1$H NMR (CD$_3$OD) δ 8.67 (s, 1H), 7.6–6.8 (m, 13H), 5.83 (d, J=2.1 Hz, 1H), 4.98 (dd, J=6.2, 2.1 Hz, 1H), 4.59 (m, 1H), 4.32 (m, 1H), 3.76 (two s, total 6H), 3.41 (s, 3H), 3.36 (m, 2H), 1.51 (s, 3H), 1.29 (s, 3H). FAB$^+$ m/z 667 (M+Na$^+$), 645 (M+H$^+$), 303 (DMT$^+$).

Compound 27. 5'-TBDMS-5-carbomethoxy-2',3'-isopropylideneuridine.

This compound was prepared as described above for the 5'-DMT protected compound, except using 5'-TBDMS-5-iodo-2',3'-isopropylideneuridine as the starting material. The product was isolated by flash chromatography on silica gel as a colorless solid. $^1$H NMR (CD$_3$OD) δ 8.58 (s, 1H), 5.71 (d, J=2.1 Hz, 1H), 4.89 (dd, J=6.2, 2.2, 1H), 4.75 (dd, J=6.0, 1.8 Hz), 4.49 (m, 1H), 3.88 (m, 2H), 3.78 (s, 3H), 1.53 (s, 3H), 1.34 (s, 3H), 0.83 (s, 9H), 0.05 (s, 3H), −0.01 (s, 3H). $^{13}$C NMR (CD$_3$OD) δ 164.9 (C4), 162.2 (COOMe), 151.3 (C2), 150.3 (C6), 114.4 (CMe$_2$), 104.4 (C5), 97.3 (C1'), 90.1 (C4'), 87.4 (C2'), 83.1 (C3'), 65.1 (C5'), 52.4 (OCH$_3$), 27.4 (CCH$_3$), 26.3 (SiC[CH$_3$]$_3$), 25.3 (CCH$_3$), 19.2 (SiC[CH$_3$]$_3$), −5.4 (SiCH$_3$), −5.5 (SiCH$_3$). HRMS: Calculated (observed) mass for C$_{20}$H$_{33}$N$_2$O$_8$Si: 457.2006(457.2006).

Compound 28. 5'-TBDMS-5-(N-histidinolcarboxyamide)-2',3'-isopropylideneuridine.

To a heavy-walled glass bomb in an argon atmosphere glove box was added 3.5 mL of a 100 mg/mL solution of 5'-DMT-2',3'-isopropylidene-5-iodouridine (0.491 mmol), 57 mg tetrakis(triphenylphosphine)palladium (0.049 1 mmol), 0.2 mL triethylamine (1.473 mmol) and 0.5 mL THF. The bomb was sealed, removed from the box and under argon was added 1.9 mL of a 100 mg/mL solution of TBDMS protected histidinol (0.736 mmol). The bomb was sealed under argon, evacuated and charged three times with 50 psi CO, and heated at 70° C. for 48 h. The bomb was allowed to cool to room temperature, vented and the solvent removed in vacuo. The crude material was purified by flash chromatography on silica gel with either a gradient of 5–7% or 0–5% MeOH/CH$_2$Cl$_2$ to give 0.294 g (69% yield) of the desired product as a white solid. $^1$H NMR (dmso-d$_6$) δ 11.9 (br s, 2H), 8.9 (d, J=8.3 Hz, 1H), 8.6 (s, 1H), 7.5 (s, 1H), 7.3 (m, 9H), 6.8 (m, 4H), 6.7 (s, 1H), 5.9 (d, J=1.3 Hz, 1H), 5.0 (dd, J=6.3, 1.4 Hz, 1H), 4.5 (unres. dd, 1H), 4.2 (m, 2H), 3.6 (m, 2H), 3.3 (m, 2H), 2.5 (m, 2H), 1.5 (s, 3H), 1.2 (s, 3H), 0.9 (s, 9H), 0.01 (s, 6H). $^{13}$C NMR (dmso-d$_6$) δ 163.2, 160.8, 158.0, 149.2, 148.0, 144.7, 135.3, 135.2, 134.7, 129.7, 129.5, 127.7, 127.5, 126.6, 113.1, 112.9, 105.2, 93.8, 86.4, 85.7, 83.9, 80.7, 63.9, 63.1, 54.9, 50.1, 28.5, 26.8, 25.7, 25.0, 17.9, −5.6, −5.6. HRMS: Calculated (observed) mass for C$_{46}$H$_{57}$N$_5$O$_{10}$Si: 867.3874(867.3884).

Compound 29. 5'-TBDMS-5-[N-(2-[4-imidazole]ethyl)carboxyamide]-2',3'-isopropylideneuridine.

To a heavy-walled glass bomb in an argon atmosphere glove box was added 2',3'-isopropylidene-5'-TBDMS-5-iodouridine (0.260 g, 0.496 mmol), 4 mL of dry THF, and tetrakis(triphenylphosphine)palladium (0.073 g, 0.063 mmol). The bomb was sealed, removed from the box and the solvent removed in vacuo. To the bomb, under argon, was then added anhydrous Et$_3$N (0.35 mL, 2.48 mmol), histamine (0.263 g, 2.37 mmol) and 2 mL of dmso-d$_6$. The bomb was evacuated and charged three times with 50 psi CO and heated at 70° C. for 2 days. After cooling to room temperature, the bomb was vented carefully and the solvents removed in vacuo at 70° C. The crude material was purified by flash chromatography on silica gel with 12% MeOH/CH2Cl2 to give 181.0 mg (68% yield) as a slightly yellow solid. $^1$H NMR (CD$_3$OD) δ 8.6 (s, 1H), 7.6 (s, 1H), 6.9 (s, 1H), 5.7 (d, J=1.9 Hz, 1H), 4.7 (dd, J=5.9, 1.6 Hz, 1H), 4.5 (m, 1H), 3.9 (m, 2H), 3.6 (m, 2H), 2.8 (t, 2H), 1.5 (s, 1H), 1.3 (s, 1H), 0.8 (s, 9H), 0.04 (s, 3H), −0.01 (s, 3H); $^{13}$C NMR (dmso-d$_6$) δ 163.2, 161.3, 149.4, 146.7, 134.7, 112.2, 111.8, 104.6, 94.6, 87.8, 84.9, 81.0, 63.4, 48.5, 27.0, 26.8, 25.6, 24.9, 17.9, −5.7; HRMS: Calculated (observed) for C$_{24}$H$_{37}$N$_5$O$_7$Si: 535.2462(535.2456). UV spectrum: λ$_{max}$ at 278 nm (ε=12930 M$^{31}$ $^1$cm$^{-1}$).

5'-Triphosphate-5-[N-(2-[4-imidazole]ethyl)carboxyamide]-2',3'-isopropylideneuridine.

The 5'-TBDMS protected histamine amide of uridine (prepared above) was desilylated with Et$_3$NH$^+$F$^-$ in CH$_3$CN for 2 days and purified on silica gel with 15% NH$_3$-MeOH/CH$_2$Cl$_2$ to give the 5'-hydroxyl histamine amide of uridine, as identified by $^1$H and $^{13}$C NMR, and FAB$^+$ mass spectrometry. This compound was used for the preparation of the 5'-triphosphate using the procedure of Eckstein. The crude triphosphate was purified successively on DEAE sephadex anion exchange resin and C18 RP-HPLC using 100 mM aq. Et$_3$NH$^+$HCO$_3^-$ and CH$_3$CN as the mobile phases. The purity of the compound was checked by analytical C18 RP-HPLC, $^1$H and $^{31}$P NMR (D$_2$O), and quantitated by its UV absorbance at 278 nm (using the ε for the nucleoside starting material, ε$_{278}$=12930 M$^{-1}$cm$^{-1}$).

Compound 30. 5'-TBDMS-5-[N-(arginine ethyl ester)carboxyamide]-2',3'-isopropylideneuridine.

To a heavy-walled glass bomb in an argon atmosphere glove box was added 2',3'-isopropylidene-5'-TBDMS-5-iodouridine (0.238 g, 0.453 mmol), arginine ethyl ester dihydrochloride (0.260 g, 0.94 mmol), tetrakis(triphenylphosphine)palladium (0.052 g, 0.045 mmol), Et$_3$N (0.32 mL, 2.3 mmol), 3 mL of dry THF, and 2 mL of DMSO. The reaction vessel was evacuated and charged with 50 psi of CO three times, then heated to 70° C. for 2 days. The crude mixture was concentrated and chromatographed on silica gel with 25% MeOH-NH₃/EtOAc to give the product as an off-white solid, 0.160 g (57% yield). ¹H NMR (CD₃OD) δ 8.55 (s, 1H), 5.64 (d, J=1.9 Hz, 1H), 4.77 (unres. dd, 1H), 4.68 (unres dd, 1H), 4.22 (q, J=7.1 Hz, 2H), 4.17 (m, 1H), 3.93 (m, 1H), 3.75 (m, 2H), 3.43 (br m, 2H), 2.0 (br m, 1H), 1.78 (br m, 3H), 1.50 (s, (s, 3H), 1.26 (t, J=7.1 Hz, 3H), 0.92 (s, 9H), 0.13 (s, 6H).

We claim:

1. A method for the preparation of a purine nucleoside modified at the 2-, 6- or 8-position of the purine ring comprising the steps of:

a) preparing a solution of a palladium catalyst, wherein said palladium catalyst is selected from the group consisting of PdL₃ or PdL₄, wherein L is a ligand of palladium;

b) reacting a purine starting material containing a halogen leaving group attached to the 2-, 6- or 8-position of said purine starting material with a nucleophile and carbon monoxide in the presence of the palladium catalyst; and c) isolating and purifying said purine nucleoside.

2. The method of claim 1 wherein said leaving group is attached to the 8-position of the purine ring.

3. The method of claim 1 wherein said purine starting material is an adenine.

4. The method of claim 3 wherein said adenine is 8-halo-adenine.

5. The method of claim 4 wherein said 8-halo-adenine is selected from the group consisting of 8-iodo-adenine and 8-bromo-adenine.

6. The method of claim 1 wherein said purine starting material is a guanine.

7. The method of claim 6 wherein said guanine is 8-halo-guanine.

8. The method of claim 7 wherein said 8-halo-guanine is selected from the group consisting of 8-iodo-guanine and 8-bromo-guanine.

9. The method of claim 1 wherein said nucleophile is selected from the group consisting of a primary amine, secondary amine and alcohol.

10. The method of claim 9 wherein said nucleophile has the formula RYH, wherein, Y is selected from the group consisting of O, NH and NR'; and R and R' are independently selected from the group consisting of a C1–C20 alkyl, C2–C20 alkenyl, C6–C20 aryl, or an amino acid, wherein R and R' are optionally part of a cyclic structure.

11. The method of claim 10 wherein R and R' are substituted with a functional group independently selected from the group consisting of an amide, ester, nitrile, nitro, urea halide, cyanate, alcohol, amine, ether, thiol and aryl.

12. The method of claim 10 wherein,

Y is selected from the group consisting of O, and NH;

R is $(CH_2)_m(CH_3)_n$, wherein z is 0, 1 or 2; m is 0–19; n is 0, 1, 2 or 3; and wherein one or more of the H are optionally replaced with =O, —OH, =NH, NH₂, N⁺Me₃Cl⁻,

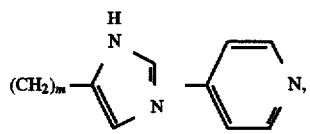

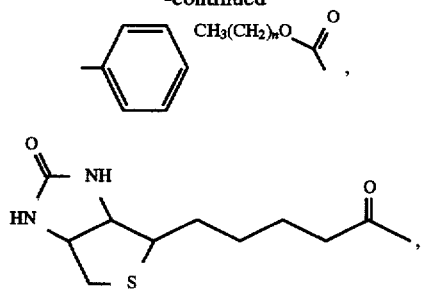

13. The method of claim 10 wherein said nucleophile is selected from the group consisting of:

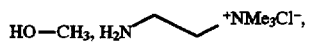

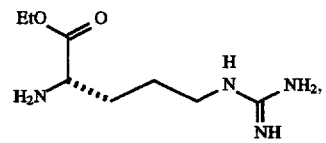

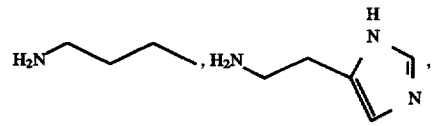

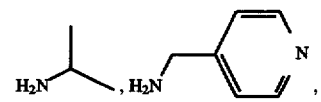

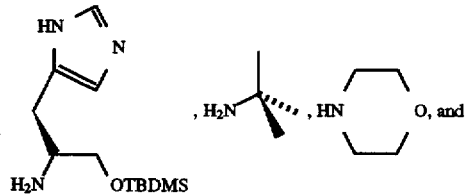

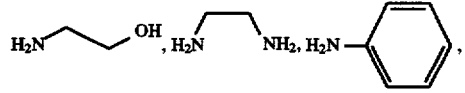

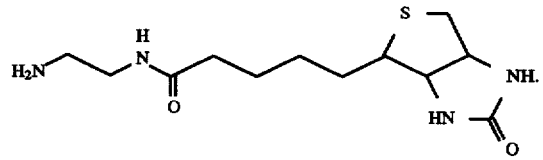

14. The method of claim 1 wherein said palladium catalyst is of the formula PdL₃ or PdL₄, wherein L is selected from the group consisting of P(C₆H₅)₃, (o-tol)₃P, CH₃CN, DMSO, N,N-dimethylformamide (DMF),

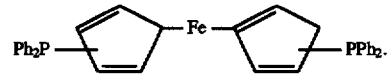

15. The method of claim 14 wherein said palladium catalyst is Pd(P(C₆H₅)₃)₄.

16. The method of claim 1 wherein the preparation of said purine nucleoside modified at the 2-, 6- or 8- position of the purine ring is performed in a solvent selected from the group consisting of THF, acetonitrile, dioxane, acetone, ethyl acetate, benzene, dimethyl formamide, dimethyl acetamide, dimethyl sulfoxide, hexamethylphosphoramide, and hexamethylphosphoroustriamide.

17. Purine nucleosides modified at the 2-, 6- or 8- position of the purine ring prepared according to the method of claim 1.

18. A method for the preparation of a pyrimidine nucleoside modified at the 5- or 6- position of the pyrimidine ring comprising the steps of:
   a) preparing a solution of a palladium catalyst, wherein said palladium catalyst is selected from the group consisting of $PdL_3$ or $PdL_4$, wherein L is a ligand of palladium;
   b) reacting a pyrimidine starting material containing a halogen leaving group attached to the 5- or 6- position of said pyrimidine starting material with a nucleophile and carbon monoxide in the presence the palladium catalyst; and
   c) isolating and purifying said pyrimidine nucleoside.

19. The method of claim 18 wherein said leaving group is attached to the 5- position of the pyrimidine ring.

20. The method of claim 18 wherein said pyrimidine starting material is a cytidine.

21. The method of claim 20 wherein said cytidine is 5-halo-cytidine.

22. The method of claim 21 wherein said 5-halo-cytidine is selected from the group consisting of 8-iodo-cytidine and 8-bromo-cytidine.

23. The method of claim 18 wherein said pyrimidine starting material is a uridine.

24. The method of claim 23 wherein said uridine is 5-halo-uridine.

25. The method of claim 24 wherein said 5-halo-uridine is selected from the group consisting of 5-iodo-uridine and 8-bromo-uridine.

26. The method of claim 18 wherein said pyrimidine starting material is a 5'-protected 5-iodo-uridine selected from the group consisting of
5'-DMT-5-iodo-2',3'-isopropylideneuridine and
5'-TBDMS-5-iodo-2',3'-isopropylideneuridine.

27. The method of claim 18 wherein said nucleophile is selected from the group consisting of an amine and an alcohol.

28. The method of claim 27 wherein said nucleophile has the formula RYH, wherein,
   Y is selected from the group consisting of O, NH and NR'; and
   R and R' are independently selected from the group consisting of a C1–C20 alkyl, C2–C20 alkenyl, C6–C20 aryl and an amino acid, wherein R and R' are optionally part of a cyclic structure.

29. The method of claim 28 wherein R and R' are substituted with a functional group independently selected from the group consisting of an amide, ester, nitrile, nitro, urea halide, cyanate, alcohol, amine, ether, thiol and aryl.

30. The method of claim 28 wherein,
   Y is selected from the group consisting of O, and NH;
   R is $(CH_2)_m(CH_3)_n$, wherein z is 0, 1 or 2; m is 0–19; n is 0, 1, 2 or 3; and wherein one or more of the H are optionally replaced with =O, —OH, =NH, $NH_2$, $N^+Me_3Cl^-$,

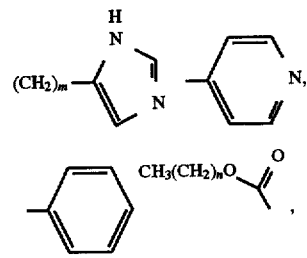

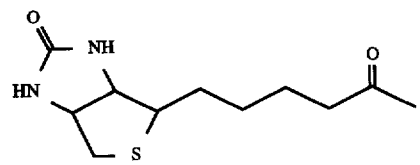

or an amino acid.

31. The method of claim 28 wherein said nucleophile is selected from the group consisting of:

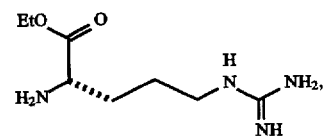

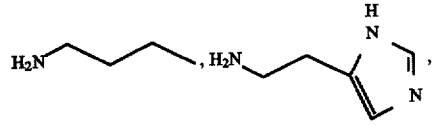

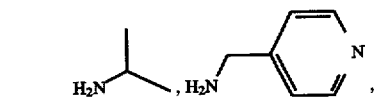

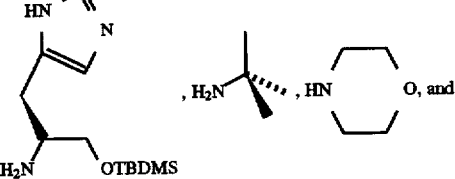

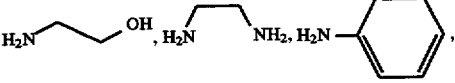

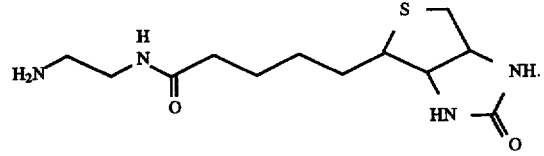

32. The method of claim 18 wherein said palladium catalyst is of the formula $PdL_3$ or $PdL_4$, wherein L is selected from the group consisting of $P(C_6H_5)_3$, (o-tol), P, $CH_3CN$, DMSO, N,N-dimethylformamide (DMF),

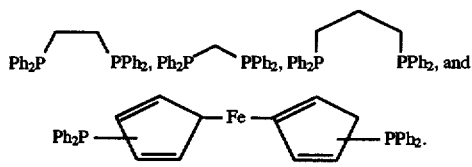

33. The method of claim 32 wherein said palladium catalyst is Pd(P(C$_6$H$_5$)$_3$)$_4$.

34. The method of claim 18 wherein the preparation of said pyrimidine nucleoside modified at the 5- or 6- position of the pyrimidine ring is performed in a solvent selected from the group consisting of THF, acetonitrile, dioxane, acetone, ethyl acetate, benzene, dimethyl formamide, dimethyl acetamide, dimethyl sulfoxide, hexamethylphosphoramide, and hexamethylphosphoroustriamide.

35. Pyrimidine nucleosides modified at the 6-position of the pyrimidine ring prepared according to the method of claim 18.

36. A compound selected from the group consisting of:

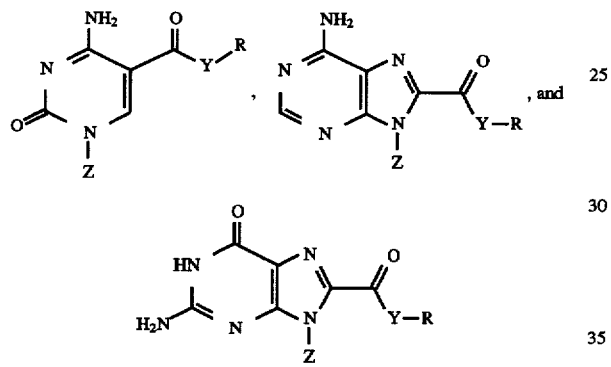

wherein,
Y is selected from the group consisting of O, NH and NR$^1$; and

R and R' are independently selected from the group consisting of a C1–C20 alkyl, C2–C20 alkenyl, aryl, and an amino acid, wherein R and R' are optionally part of a cyclic structure selected from an aromatic, aliphatic, or heterocyclic; and Z is selected from the group consisting of a ribose, deoxyribose, and dideoxyribose.

37. The method of claim 36 wherein R and R' are substituted with a functional group independently selected from the group consisting of an amide, ester, nitrile, nitro, urea halide, cyanate, alcohol, amine, ether, thiol and aryl.

38. A compound of claim 36 wherein,

Y is selected from the group consisting of O and NH;

R is (CH$_2$)$_m$(CH$_3$)$_n$, wherein z is 0, 1 or 2; m is 0–19; n is 1, 2 or 3; and wherein one or more of the H are optionally replaced with =O, —OH, =NH, NH$_2$, N$^+$Me$_3$Cl$^-$,

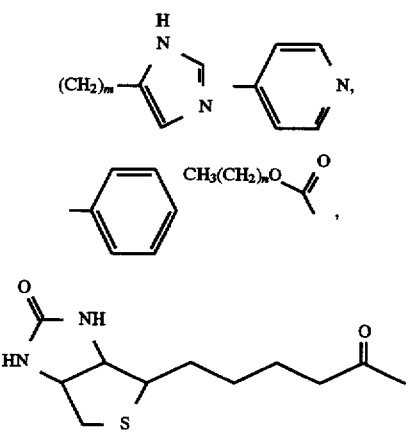

or an amino acid.

39. A compound selected from the group consisting of:

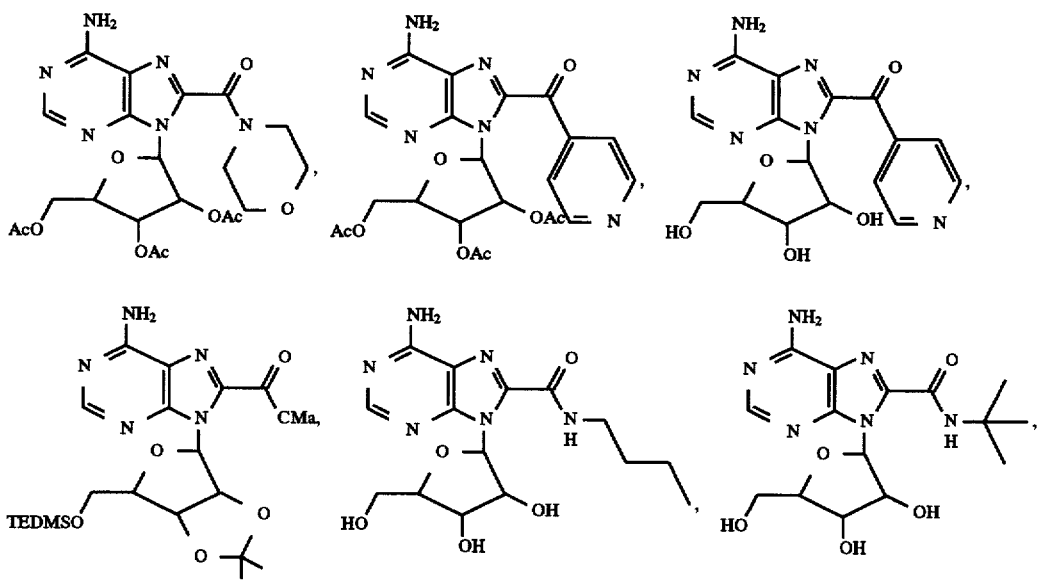

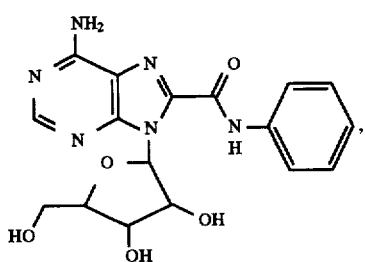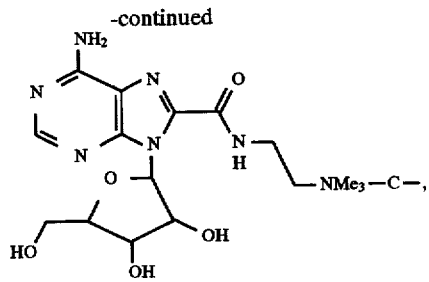
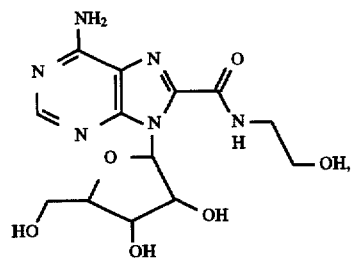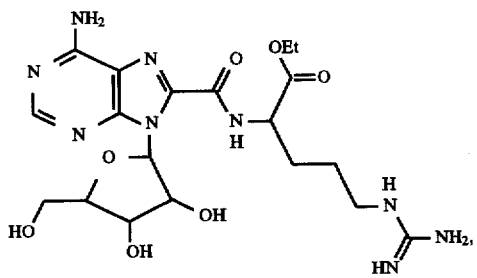
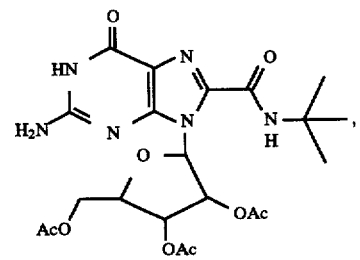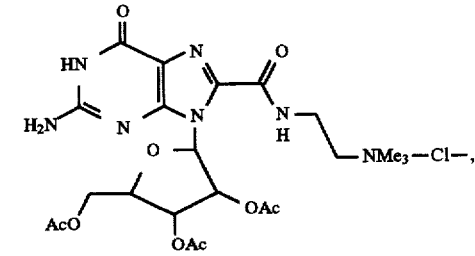
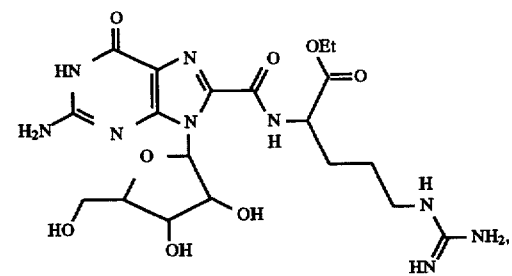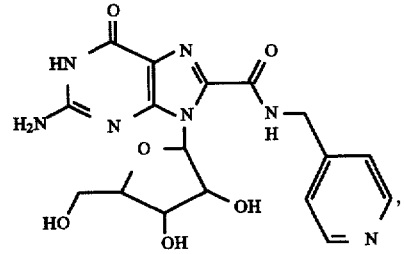
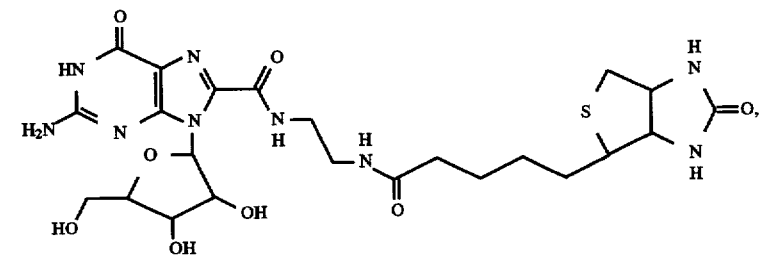
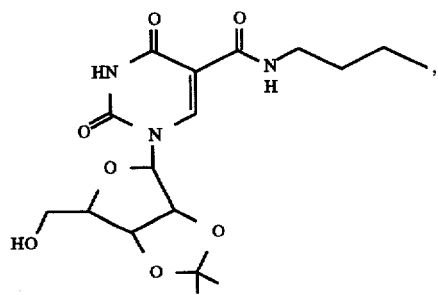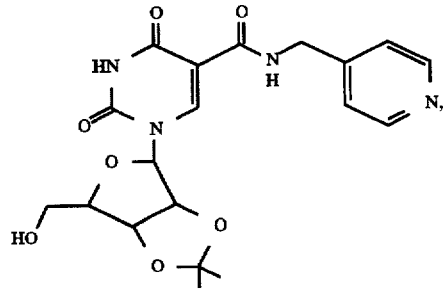

-continued
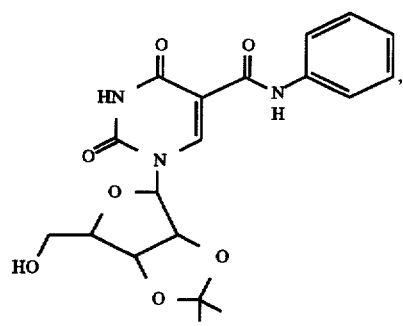 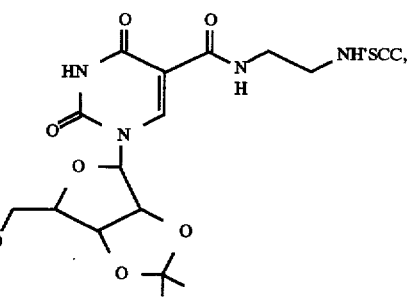
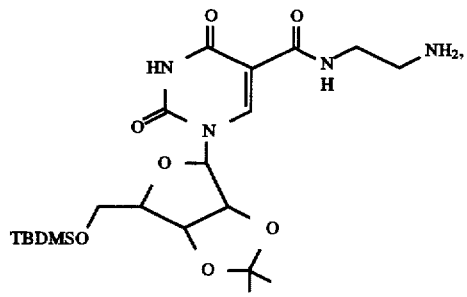 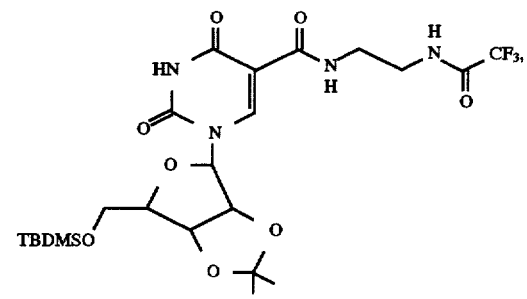
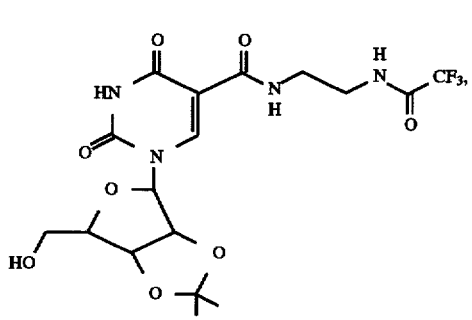 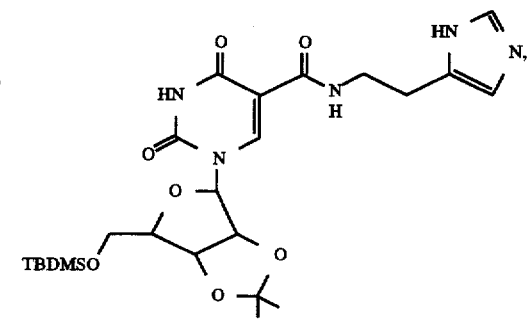
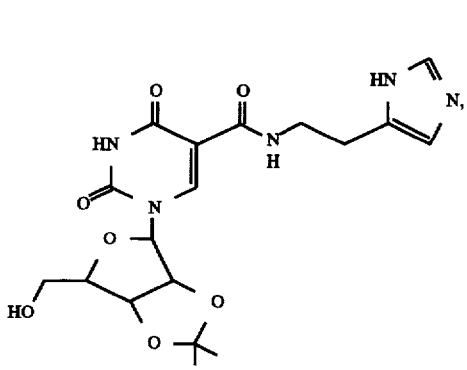 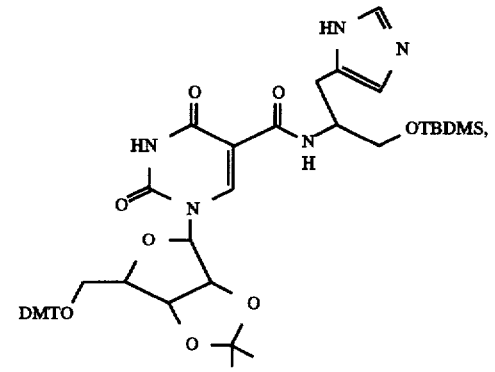
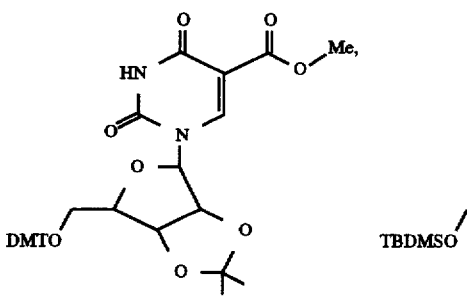 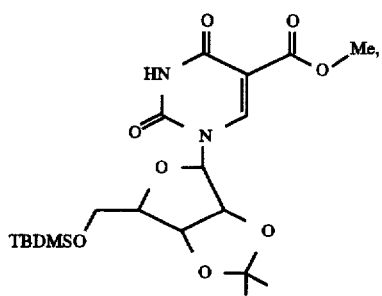

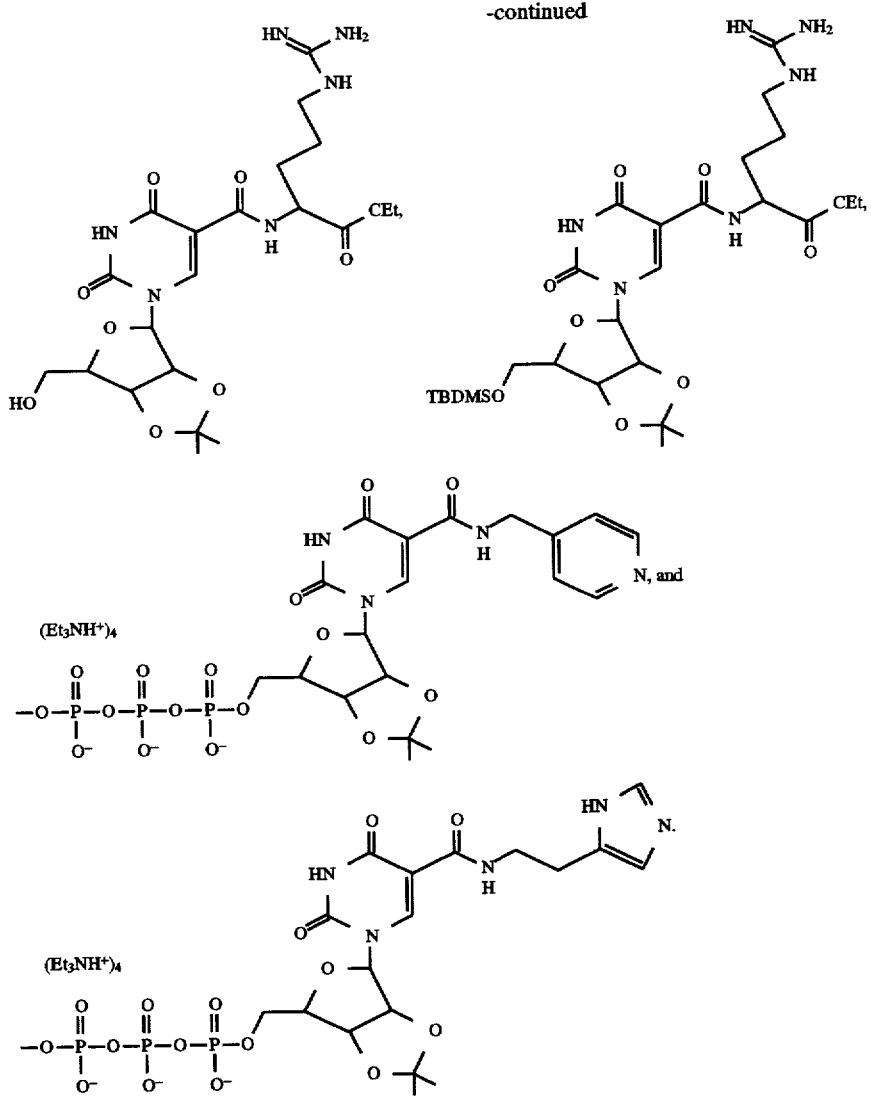

40. The modified nucleoside of claim 17 wherein said purine is selected from the group consisting of an adenine and a guanine.

41. The modified nucleoside of claim 35 wherein said pyrimidine is selected from the group consisting of a uridine and a cytidine.

42. A compound selected from the group consisting of:

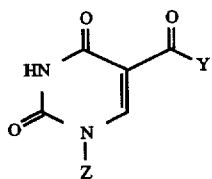

wherein,

Y is selected from the group consisting of SR', NHR' and NR'R";

R' and R" are independently selected from the group consisting a C1–C20 alkyl, C2–20 alkenyl, aryl, natural amino acids and unnatural amino acids, wherein R' and R" can optionally be part of a cyclic structure which can be aromatic, aliphatic, or heterocyclic; and Z is selected from the group consisting of a ribose, deoxyribose and dideoxyribose.

43. A compound of claim 42 wherein,

Y is selected from the group consisting of SR', and NHR';

R' is $(CH_2)_m(CH_3)_n$, wherein z is 0, 1, or 2; m is 0–19; n is 1, 2, or 3; and wherein one or more of the H atom(s) are optionally replaced with =O, —OH, =NH, $NH_2$, $+NMe_3Cl$, or an amino acid.

* * * * *

UNITED STATES PATENT AND TRADEMARK OFFICE
CERTIFICATE OF CORRECTION

PATENT NO. : 5,719,273
DATED : February 17, 1998
INVENTOR(S) : Chi Tu, Torin M. Dewey and Bruce Eaton It is certified that error appears in the above-identified patent and that said Letters Patent is hereby corrected as shown below:

IN THE CLAIMS:

22. The method of claim 21 wherein said 5-halo-cytidine is selected from the group consisting of 5-iodo-cytidine and 5-bromo-cytidine.

25. The method of claim 24 wherein said 5-halo-uridine is selected from the group consisting of 5-iodo-uridine and 5-bromo-uridine.

37. The compound of claim 36 wherein R and R' are substituted with a functional group independently selected from the group consisting of an amide, ester, nitrile, nitro, urea, halide, cyanate, alcohol, amine, ether, thiol and aryl.

Signed and Sealed this

Fifteenth Day of December, 1998

*Attest:*

BRUCE LEHMAN

*Attesting Officer*     *Commissioner of Patents and Trademarks*